United States Patent
Li et al.

(10) Patent No.: US 10,577,345 B2
(45) Date of Patent: *Mar. 3, 2020

(54) PROCESS FOR SYNTHESIZING 2-HYDROXY-6-((2-(1-ISOPROPYL-1H-PYRAZOL-5-YL)-PYRIDIN-3-YL)METHOXY)BENZALDEHYDE

(71) Applicant: Global Blood Therapeutics, Inc., South San Francisco, CA (US)

(72) Inventors: Zhe Li, San Diego, CA (US); Nathan Guz, Half Moon Bay, CA (US); Yiyang Shao, Beijing (CN); Julieana Cocuz, Neutraubling (DE); Markus Frieser, Maxhütte-Haidhof (DE); George Petros Yiannikouros, Florence, SC (US); Liang Liao, Pleasanton, CA (US)

(73) Assignee: Global Blood Therapeutics, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/101,251

(22) Filed: Aug. 10, 2018

(65) Prior Publication Data

US 2019/0106404 A1    Apr. 11, 2019

Related U.S. Application Data

(63) Continuation of application No. 15/593,198, filed on May 11, 2017, now Pat. No. 10,077,249.

(60) Provisional application No. 62/335,583, filed on May 12, 2016.

(51) Int. Cl.
  *C07D 401/04* (2006.01)
  *C07C 45/65* (2006.01)
  *C07C 47/575* (2006.01)

(52) U.S. Cl.
  CPC ............ *C07D 401/04* (2013.01); *C07C 45/65* (2013.01); *C07C 47/575* (2013.01); *C07B 2200/13* (2013.01)

(58) Field of Classification Search
  CPC .................................................. C07D 401/04
  USPC ..................................................... 546/275.4
  See application file for complete search history.

(56) References Cited

U.S. PATENT DOCUMENTS

| | | |
|---|---|---|
| 3,236,893 A | 2/1966 | Blout et al. |
| 4,062,858 A | 12/1977 | Hoehn et al. |
| 4,410,537 A | 10/1983 | Kneen |
| 4,478,834 A | 10/1984 | Shroff et al. |
| 4,535,183 A | 8/1985 | Kneen |
| 5,185,251 A | 2/1993 | Chen et al. |
| 5,202,243 A | 4/1993 | Balani |
| 5,266,582 A | 11/1993 | De Nanteuil et al. |
| 5,290,941 A | 3/1994 | Volante et al. |
| 5,403,816 A | 4/1995 | Takabe et al. |
| 5,521,202 A | 5/1996 | Yano et al. |
| 5,679,678 A | 10/1997 | Binder et al. |
| 5,681,567 A | 10/1997 | Martinez et al. |
| 5,760,232 A | 6/1998 | Chen et al. |
| 5,840,900 A | 11/1998 | Greenwald et al. |
| 5,880,131 A | 3/1999 | Greenwald et al. |
| 5,965,566 A | 10/1999 | Greenwald et al. |
| 5,994,353 A | 11/1999 | Breault |
| 6,011,042 A | 1/2000 | Greenwald et al. |
| 6,111,107 A | 8/2000 | Greenwald et al. |
| 6,127,355 A | 10/2000 | Greenwald et al. |
| 6,153,655 A | 10/2000 | Martinez et al. |
| 6,194,580 B1 | 2/2001 | Greenwald et al. |
| 6,214,817 B1 | 4/2001 | Riley et al. |
| 6,232,320 B1 | 5/2001 | Stewart et al. |
| 6,239,176 B1 | 5/2001 | Nudelman et al. |
| 6,242,644 B1 | 6/2001 | Ackermann et al. |
| 6,355,661 B1 | 3/2002 | Lai et al. |
| 6,395,266 B1 | 5/2002 | Martinez et al. |
| 6,472,349 B1 | 10/2002 | Hamprecht et al. |
| 6,593,472 B2 | 7/2003 | Hoffman et al. |
| 6,608,076 B1 | 8/2003 | Greenwald et al. |
| 6,627,646 B2 | 9/2003 | Bakale |
| 6,630,496 B1 | 10/2003 | Seehra et al. |
| 6,670,377 B1 | 12/2003 | Mekouar et al. |
| 7,160,910 B2 | 1/2007 | Safo et al. |
| 7,411,083 B2 | 8/2008 | Gopalsamy et al. |
| 8,846,694 B2 | 9/2014 | Heinrich et al. |
| 8,952,171 B2 | 2/2015 | Xu et al. |
| 9,012,450 B2 | 4/2015 | Metcalf et al. |
| 9,018,210 B2 | 4/2015 | Metcalf et al. |
| 9,150,569 B2 | 10/2015 | Fukuda et al. |
| 9,248,199 B2 | 2/2016 | Metcalf et al. |
| 9,422,279 B2 | 8/2016 | Metcalf et al. |
| 9,447,071 B2 | 9/2016 | Li et al. |

(Continued)

FOREIGN PATENT DOCUMENTS

| | | |
|---|---|---|
| CA | 2720096 | 10/2009 |
| CN | 101113148 | 1/2008 |

(Continued)

OTHER PUBLICATIONS

U.S. Appl. No. 61/581,053, filed Dec. 28, 2011, Metcalf et al.
U.S. Appl. No. 61/661,320, filed Jun. 18, 2012, Metcalf et al.
Abdulmalik et al., "Crystallographic analysis of human hemoglobin elucidates the structural basis of the potent and dual antisickling activity of pyridyl derivatives of vanillin", Acta Cryst. 2011, D67, 920-928.

(Continued)

*Primary Examiner* — Taofiq A Solola
(74) *Attorney, Agent, or Firm* — Sheppard Mullin Richter & Hampton LLP (57) ABSTRACT

Disclosed herein are processes for synthesizing 2-hydroxy-6-((2-(1-isopropyl-1H-pyrazol-5-yl)-pyridin-3-yl)methoxy)benzaldehyde (also referred to herein as Compound (I)) and intermediates used in such processes. Compound (I) binds to hemoglobin and increases it oxygen affinity and hence can be useful for the treatment of diseases such as sickle cell disease.

17 Claims, 2 Drawing Sheets

(56) References Cited

U.S. PATENT DOCUMENTS

| | | | |
|---|---|---|---|
| 9,458,139 B2 | 10/2016 | Xu et al. |
| 9,604,999 B2 | 3/2017 | Harris et al. |
| 9,776,960 B2 | 10/2017 | Xu et al. |
| 9,802,900 B2 | 10/2017 | Li et al. |
| 10,017,491 B2 | 7/2018 | Metcalf et al. |
| 10,034,879 B2 | 7/2018 | Metcalf et al. |
| 10,137,118 B2 | 11/2018 | Li et al. |
| 2001/0046997 A1 | 11/2001 | Abraham et al. |
| 2002/0095035 A1 | 7/2002 | Warshawsky et al. |
| 2002/0142995 A1 | 10/2002 | Nicolau et al. |
| 2002/0147138 A1 | 10/2002 | Firestone et al. |
| 2003/0022923 A1 | 1/2003 | Lai et al. |
| 2003/0060425 A1 | 3/2003 | Ahlem et al. |
| 2003/0073712 A1 | 4/2003 | Wang et al. |
| 2003/0165714 A1 | 9/2003 | Lee et al. |
| 2003/0187026 A1 | 10/2003 | Li et al. |
| 2003/0190333 A1 | 10/2003 | Mossman et al. |
| 2003/0199511 A1 | 10/2003 | Li et al. |
| 2004/0072796 A1 | 4/2004 | Embury et al. |
| 2004/0186077 A1 | 9/2004 | Diakur et al. |
| 2004/0209921 A1 | 10/2004 | Bridger et al. |
| 2005/0085484 A1 | 4/2005 | Mitchell et al. |
| 2005/0096337 A1 | 5/2005 | Ackermann et al. |
| 2005/0143420 A1 | 6/2005 | Moutouh-De Parseval et al. |
| 2005/0159605 A1 | 7/2005 | Tarur et al. |
| 2006/0094761 A1 | 5/2006 | Haque et al. |
| 2007/0213323 A1 | 9/2007 | Imogai et al. |
| 2007/0293698 A1 | 12/2007 | Quick et al. |
| 2008/0114167 A1 | 5/2008 | Castro et al. |
| 2009/0023709 A1 | 1/2009 | Gillespie et al. |
| 2009/0143371 A1 | 6/2009 | Buettelmann |
| 2009/0163512 A1 | 6/2009 | Chen et al. |
| 2009/0312315 A1 | 12/2009 | Yamaguchi et al. |
| 2010/0048901 A1 | 2/2010 | Takahashi et al. |
| 2010/0204235 A1 | 8/2010 | Lizos et al. |
| 2010/0210651 A1 | 8/2010 | Hernandez et al. |
| 2010/0311748 A1 | 12/2010 | Dakin et al. |
| 2012/0220569 A1 | 8/2012 | Ohashi et al. |
| 2012/0245344 A1 | 9/2012 | Endo et al. |
| 2013/0045251 A1 | 2/2013 | Cen et al. |
| 2013/0072472 A1 | 3/2013 | Gless et al. |
| 2013/0190315 A1 | 7/2013 | Metcalf et al. |
| 2013/0190316 A1 | 7/2013 | Metcalf et al. |
| 2013/0190375 A1 | 7/2013 | Dunkel et al. |
| 2013/0273157 A1 | 10/2013 | Ishii et al. |
| 2014/0004184 A1 | 1/2014 | Ashraf et al. |
| 2014/0142149 A1 | 5/2014 | Zhang et al. |
| 2014/0271591 A1 | 9/2014 | Sinha et al. |
| 2014/0274961 A1 | 9/2014 | Metcalf et al. |
| 2014/0275152 A1 | 9/2014 | Metcalf et al. |
| 2014/0275176 A1 | 9/2014 | Xu et al. |
| 2014/0275181 A1 | 9/2014 | Harris et al. |
| 2015/0057251 A1 | 2/2015 | Harris |
| 2015/0133430 A1 | 5/2015 | Xu et al. |
| 2015/0141465 A1 | 5/2015 | Yee et al. |
| 2015/0225366 A1 | 8/2015 | Li |
| 2015/0259296 A1 | 9/2015 | Li et al. |
| 2015/0336908 A1 | 11/2015 | Shioda et al. |
| 2015/0344472 A1 | 12/2015 | Metcalf et al. |
| 2015/0344483 A1 | 12/2015 | Metcalf et al. |
| 2016/0024127 A1 | 1/2016 | Harris et al. |
| 2016/0031865 A1 | 2/2016 | Li et al. |
| 2016/0031904 A1 | 2/2016 | Li et al. |
| 2016/0038474 A1 | 2/2016 | Sinha et al. |
| 2016/0039801 A1 | 2/2016 | Metcalf et al. |
| 2016/0046613 A1 | 2/2016 | Metcalf et al. |
| 2016/0083343 A1 | 3/2016 | Xu et al. |
| 2016/0303099 A1 | 3/2016 | Dufu et al. |
| 2016/0152602 A1 | 6/2016 | Xu et al. |
| 2016/0206604 A1 | 7/2016 | Metcalf et al. |
| 2016/0206614 A1 | 7/2016 | Metcalf et al. |
| 2016/0207904 A1 | 7/2016 | Li et al. |
| 2016/0332984 A1 | 11/2016 | Metcalf et al. |
| 2016/0346263 A1 | 12/2016 | Li et al. |
| 2017/0107199 A1 | 4/2017 | Metcalf et al. |
| 2017/0157101 A1 | 6/2017 | Ramos et al. |
| 2017/0174654 A1 | 6/2017 | Metcalf et al. |
| 2017/0355713 A1 | 12/2017 | Harris et al. |
| 2018/0125789 A1 | 5/2018 | Dalziel et al. |
| 2018/0186807 A1 | 7/2018 | Yee et al. |
| 2018/0201577 A1 | 7/2018 | Xu et al. |
| 2018/0354929 A1 | 12/2018 | Metcalf et al. |
| 2019/0010121 A1 | 1/2019 | Xu et al. |
| 2019/0010176 A1 | 1/2019 | Harris |
| 2019/0106404 A1 | 4/2019 | Li et al. |
| 2019/0111037 A1 | 4/2019 | Li et al. |
| 2019/0112287 A1 | 4/2019 | Metcalf et al. |
| 2019/0160060 A1 | 5/2019 | Metcalf et al. |
| 2019/0202782 A1 | 7/2019 | Xu et al. |
| 2019/0255031 A1 | 8/2019 | Li et al. |

FOREIGN PATENT DOCUMENTS

| | | |
|---|---|---|
| CN | 102116772 | 7/2011 |
| DE | 2238734 | 2/1973 |
| DE | 2238628 | 3/1973 |
| DE | 2853765 | 6/1980 |
| DE | 2904829 | 8/1980 |
| DE | 226590 | 8/1985 |
| DE | 3503435 | 8/1985 |
| DE | 3431004 | 3/1986 |
| DE | 3704223 | 8/1987 |
| DE | 258226 | 7/1988 |
| DE | 276479 | 2/1990 |
| DE | 276480 | 2/1990 |
| DE | 3931954 | 3/1990 |
| DE | 4318550 | 12/1994 |
| DE | 4442050 | 5/1996 |
| EP | 010063 | 4/1980 |
| EP | 0054924 | 6/1982 |
| EP | 236140 | 9/1987 |
| EP | 0268989 | 6/1988 |
| EP | 0278686 | 8/1988 |
| EP | 0291916 | 11/1988 |
| EP | 0303465 | 2/1989 |
| EP | 0336369 | 10/1989 |
| EP | 0348155 | 12/1989 |
| EP | 0365328 | 4/1990 |
| EP | 0401517 | 12/1990 |
| EP | 0453210 | 10/1991 |
| EP | 0462800 | 12/1991 |
| EP | 0481802 | 4/1992 |
| EP | 0498380 | 8/1992 |
| EP | 0528337 | 2/1993 |
| EP | 0542372 | 5/1993 |
| EP | 0567133 | 10/1993 |
| EP | 0632036 | 1/1995 |
| EP | 0637586 | 2/1995 |
| EP | 0640609 | 3/1995 |
| EP | 0747393 | 12/1996 |
| EP | 2123637 | 11/2009 |
| EP | 2149545 | 3/2010 |
| EP | 2305625 | 6/2011 |
| FR | 2217016 | 1/1900 |
| FR | 2909379 | 6/2008 |
| GB | 1409865 | 10/1975 |
| GB | 1593417 | 7/1981 |
| IL | 64573 | 4/1985 |
| JP | 57-145844 | 6/1905 |
| JP | 59029667 | 2/1984 |
| JP | 61-040236 | 2/1986 |
| JP | 63230687 | 9/1988 |
| JP | S-63258463 | 10/1988 |
| JP | 01190688 | 7/1989 |
| JP | 06-041118 | 2/1994 |
| JP | 07-025882 | 1/1995 |
| JP | 2002-523469 | 7/2002 |
| JP | 2002-528537 | 9/2002 |
| JP | 2003-075970 | 3/2003 |
| JP | 2003-513060 | 4/2003 |
| JP | 2006-342115 | 12/2006 |
| JP | 2008-137914 | 6/2008 |
| JP | 2009-203230 | 9/2009 |
| WO | WO-91/19697 | 12/1991 |

(56) References Cited

FOREIGN PATENT DOCUMENTS

| | | |
|---|---|---|
| WO | WO-92/02503 | 2/1992 |
| WO | WO-93/17013 | 9/1993 |
| WO | WO-94/01406 | 1/1994 |
| WO | WO-95/14015 | 5/1995 |
| WO | WO-95/21854 | 8/1995 |
| WO | WO-96/11902 | 4/1996 |
| WO | WO-97/41120 | 11/1997 |
| WO | WO-97/44306 | 11/1997 |
| WO | WO-98/08818 | 3/1998 |
| WO | WO-98/21199 | 5/1998 |
| WO | WO-99/29694 | 6/1999 |
| WO | WO-99/43672 | 9/1999 |
| WO | WO-99/47529 | 9/1999 |
| WO | WO-99/48490 | 9/1999 |
| WO | WO-99/59978 | 11/1999 |
| WO | WO-99/62908 | 12/1999 |
| WO | WO-00/12121 | 3/2000 |
| WO | WO-00/26202 | 5/2000 |
| WO | WO-00/35858 | 6/2000 |
| WO | WO-00/40564 | 7/2000 |
| WO | WO-00/71123 A1 | 11/2000 |
| WO | WO-00/75145 | 12/2000 |
| WO | WO-00/78746 | 12/2000 |
| WO | WO-01/00612 | 1/2001 |
| WO | WO-01/19823 | 3/2001 |
| WO | WO-01/23383 | 4/2001 |
| WO | WO-01/32596 | 5/2001 |
| WO | WO-01/36375 | 5/2001 |
| WO | WO-01/57006 | 8/2001 |
| WO | WO-01/57044 | 8/2001 |
| WO | WO-01/62705 | 8/2001 |
| WO | WO-01/70663 | 9/2001 |
| WO | WO-02/00622 | 1/2002 |
| WO | WO-02/12235 | 2/2002 |
| WO | WO-02/24635 | 3/2002 |
| WO | WO-02/24679 | 3/2002 |
| WO | WO-02/051849 | 7/2002 |
| WO | WO-02/053547 | 7/2002 |
| WO | WO-02/061849 | 8/2002 |
| WO | WO-03/051366 | 6/2003 |
| WO | WO-03/053368 | 7/2003 |
| WO | WO-03/101959 | 12/2003 |
| WO | WO-2004/014899 | 2/2004 |
| WO | WO-2004/018430 | 3/2004 |
| WO | WO-2004/024705 | 3/2004 |
| WO | WO-2004/050030 | 6/2004 |
| WO | WO-2004/056727 | 7/2004 |
| WO | WO-2004/058790 | 7/2004 |
| WO | WO 2004/073675 | 9/2004 |
| WO | WO-2004/087075 | 10/2004 |
| WO | WO-2004/111031 | 12/2004 |
| WO | WO-2005/047249 | 5/2005 |
| WO | WO-2005/074513 | 8/2005 |
| WO | WO-2005/077932 | 8/2005 |
| WO | WO-2005/086951 | 9/2005 |
| WO | WO-2005/087766 | 9/2005 |
| WO | WO-2005/096337 | 10/2005 |
| WO | WO-2006/011469 | 2/2006 |
| WO | WO-2006/065204 | 6/2006 |
| WO | WO-2006/088173 | 8/2006 |
| WO | WO-2006/103463 | 10/2006 |
| WO | WO-2006/106711 | 10/2006 |
| WO | WO-2006/116764 | 11/2006 |
| WO | WO-2006/003923 | 12/2006 |
| WO | WO-2007/003962 | 1/2007 |
| WO | WO-2007/009389 | 1/2007 |
| WO | WO-2007/017267 | 2/2007 |
| WO | WO-2007/047204 | 4/2007 |
| WO | WO-2007/049675 | 5/2007 |
| WO | WO-2007/061923 | 5/2007 |
| WO | WO-2007/084914 | 7/2007 |
| WO | WO-2007/117180 | 10/2007 |
| WO | WO 2008/012495 | 1/2008 |
| WO | WO-2008/013414 | 1/2008 |
| WO | WO-2008/016132 | 2/2008 |
| WO | WO-2008/029200 | 3/2008 |
| WO | WO-2008/041118 | 4/2008 |
| WO | WO-2008/051532 | 5/2008 |
| WO | WO-2008/060391 | 5/2008 |
| WO | WO-2008/066145 | 6/2008 |
| WO | WO-2008/081096 | 7/2008 |
| WO | WO-2008/101682 | 8/2008 |
| WO | WO-2008/116620 | 10/2008 |
| WO | WO-2009/001214 | 12/2008 |
| WO | WO-2009/011850 | 1/2009 |
| WO | WO-2009/050183 | 4/2009 |
| WO | WO-2009/125606 | 10/2009 |
| WO | WO-2009/128537 | 10/2009 |
| WO | WO-2009/130560 | 10/2009 |
| WO | WO-2009/136889 | 11/2009 |
| WO | WO-2009/146555 | 12/2009 |
| WO | WO 2009/153191 | 12/2009 |
| WO | WO-2010/031589 | 3/2010 |
| WO | WO-2010/056631 | 5/2010 |
| WO | WO-2010/129055 | 11/2010 |
| WO | WO-2011/033045 | 3/2011 |
| WO | WO-2011/088201 | 7/2011 |
| WO | WO-2011/136459 | 11/2011 |
| WO | WO-2012/020060 | 2/2012 |
| WO | WO-2012/138981 | 10/2012 |
| WO | WO-2012/141228 | 10/2012 |
| WO | WO-2013/052803 | 4/2013 |
| WO | WO-2013/102142 | 7/2013 |
| WO | WO-2013/102145 | 7/2013 |
| WO | WO-2014/104384 | 7/2014 |
| WO | WO-2014/150256 | 9/2014 |
| WO | WO-2014/150258 | 9/2014 |
| WO | WO-2014/150261 | 9/2014 |
| WO | WO-2014/150268 | 9/2014 |
| WO | WO-2014/150276 | 9/2014 |
| WO | WO-2014/150289 | 9/2014 |
| WO | WO-2015/031284 | 3/2015 |
| WO | WO-2015/031285 | 3/2015 |
| WO | WO-2015/120133 | 8/2015 |
| WO | WO-2016/160755 | 10/2016 |
| WO | WO-2017/096230 | 6/2017 |

OTHER PUBLICATIONS

Abdulmalik et al., Sickle cell disease: current therapeutic approaches, Expert Opinion Ther. Patents, 2005, vol. 15(11), pp. 1497-1506.

Abraham et al., Vanillin, a Potential Agent for the Treatment of Sickle Cell Anemia, Blood, Mar. 1991, vol. 77 (6), pp. 1334-1341.

Adhikary, P.K., et al., "A new antisickling agent: In vitro studies of its effect on S/S erythrocytes and on hemoglobin S", Experientia. 1978, vol. 34, No. 6, pp. 804-806.

Appendix A provided with Israel office action dated Aug. 11, 2016 for IL 233329.

Arya R, et al. "Tucaresol increases oxygen affinity and reduces haemolysis in subjects with sickle cell anaemia," Br. J. Haematol., 93(4):817-21 (1996).

Australian Examination Report dated Nov. 7, 2016 for AU 2016203755.

Babu, et al. Regioselective synthesis and structural elucidation of 1,4-disubstituted 1,2,3-triazole derivatives using 1D and 2D NMR spectral techniques. Magn. Reson. Chem., 2011; 49: 824-829. doi:10.1002/mrc.2820.

Bacsa et al., "Novel products from Baylis-Hillman reactions of salicylaldehydes", South African Journal of Chemistry (1998), 51(1), 47-54 CODEN: SAJCDG; ISSN: 0379-4350.

Ballerini et al., High pressure Diels-Alder approach to hydroxy-substituted 6a-cyano-tetrahydro-6H-benzo[c]chromen-6-ones: A route to Δ6-Cis-Cannabidiol. J.Org.Chem., 74(11):4311-4317, 2009.

Ballet et al., Novel selective human melanocortin-3 receptor ligands: Use of the 4-amino-1,2,4,5-tetrahydro-2-benzazepin-3- one (Aba) scaffold, Bioorganic & Medicinal Chemistry Letters (2007), 17(9), 2492-2498 CODEN: BMCLES; ISSN: 0960-894X.

Barnes, et al., "Prospects for new drugs for chronic obstructive pulmonary disease." The Lancet, 2004, 364, 985-996.

Barnes. "COPD: is there light at the end of the tunnel?" Current Opinion in Pharmacology, 2004, 4:263-272.

(56) References Cited

OTHER PUBLICATIONS

Baxter et al., "Reductive aminations of carbonyl compounds with borohydride and borane reducing agents", Organic Reactions (Hoboken, NJ, United States) (2002), 59, No pp. given bin/mrwhome/107610747/HOME.
Beaumont et al., Design of ester prodrugs to enhance oral absorption of poorly permeable compounds: challenges to the discovery scientist. Curr. Drug Metab. 2003, 4:461-85.
Beddell, Substituted benzaldehydes designed to increase the oxygen affinity of human haemoglobin and inhibit the sickling of sickle erythrocycles, Br. J. Pharmac., 82:397-407, 1984.
Beena et al., "Synthesis and antibacterial activity evaluation of metronidazole-triazole conjugates", Bioorganic & Medicinal Chemistry Letters, 2009, 19(5):1396-1398.
Behanna. Equity Research—Global Blood Therapeutics. Sep. 8, 2015. Retrieved from the Internet: URL:http://www.fintechsecurities.com/Websites/fintechsecurities/images/Research_Blog/Zacks/Sep2015/GBT150908.pdf.
Berge et al., "Pharmaceutical Salts", Journal of Pharmaceutical Science, 1977, 66:1-19.
Bernstein. Crystals in Supramolecular Chemistry. ACA Transactions. 2004; 39:1-14.
Bernstein. Polymorphism in Molecular Crystals. Clarendon Press, Oxford. 2002. 115-118, 272.
Bode et al.,"Novel synthesis and x-ray crystal structure of a coumarin derivative", South African Journal of Chemistry (1992), 45(1), 25-7 CODEN: SAJCDG; ISSN:0379-4350.
Bonaventura, et al., "Molecular Controls of the Oxygenation and Redox Reactions of Hemoglobin." Antioxidants & Redox Signaling, 18(17), 2013, 2298-2313.
Bottino, et al. Study on the scope of tert-amino effect: new extensions of type 2 reactions to bridged biaryls. J. Phys. Org. Chem. 2012; 25(11):1033-1041.
Bradbury et al., "New nonpeptide angiotensin II receptor antagonists", Journal of Medicinal Chemistry, 1993, vol. 36, pp. 1245-1254.
Braga, et al. Making crystals from crystals: a green route to crystal engineering and polymorphism. Chem Commun (Camb). Aug. 7, 2005;(29):3635-45. Epub Jun. 15, 2005.
Britton et al., "Structure-activity relationships of a series of benzothlophens-derived NPY Y1 antagonists: optimization of the C-2 side chain". Bioorganic & Medicinal Chemistry Letters (1999), 9(3), 475-480 CODEN:BMCLE8;ISSN: 0960-894X.
Brown et al., "1,2-Dihydroisoquinollnes. III, Dimerization", Tetrahedron (1966), 22(8), 2437-43 CODEN: TETRAB; ISSN;0040-4020.
Caira. Crystalline Polymorphism of Organic Compounds. Topics in Current Chemistry, Springer, Berlin, DE. 1998; 198:163-208.
CAS Registry No. 1039841-20-7; entry dated Aug. 10, 2008.
CAS Registry No. 1096911-11-3; entry dated Jan. 28, 2009.
CAS Registry No. 1153166-41-6; entry dated Jun. 7, 2009.
CAS Registry No. 1153961-01-3; entry dated Jun. 8, 2009.
CAS Registry No. 1184809-65-1; entry dated Sep. 15, 2009.
CAS Registry No. 1303782-57-1; entry dated Jun. 1, 2011.
CAS Registry No. 1306264-96-9; entry dated Jun. 5, 2011.
CAS Registry No. 631858-40-7; entry dated Dec. 29, 2003.
Chemical Abstract Registry No. 1142191-55-6, indexed in the Registry File on STN CA Online May 4, 2009.
Cheng, et al. Vilsmeier formylation of tert-anilines: dibenzo[b,f][1,5]diazocines and quinazolinium salts via the 't-amino effect'. J. Chem. Soc., Perkin Trans 1. 1998; 1257-1262.
Cherian et al., "Structure-Activity Relationships of Antitubercular Nitroimidazoles 3. Exploration of the Linker and Lipophilic Tail of ((S)-2-Nitro-6,7-dihydro-5H-imidazo[2,1-13][1,3]oxazin-6-yl)-(4-trifluoromethoxybenzyl)amine (6-Amino PA-824).," J. Med. Chem., Aug. 2011, vol. 54(16), pp. 5639-5659.
Ciganek, "The catalyzed a-hydroxyalkylation and a-aminoalkylation of activated olefins (the Morita-Baylis-Hillman reaction)", Organic Reactions (Hoboken, NJ, United States) (1997), 51, No pp given CODEN:ORHNBA URL:http://www3.Interscience.wiley.com/cgi-bin/mnwhome/107610747/HOME.
CMU Pharmaceutical polymorphism, internet p. 1-3 (2002) printout Apr. 3, 2008.
Concise Encyclopedia Chemistry, NY: Walter de Gruyter, 1993, 872-873.
Congreve et al. Application of Fragment Screening by X-ray Crystallography to the Discovery of Aminopyridines as Inhibitors of Beta-Secretase. J. Med. Chem. 50:1124-1132 (2007).
Cos et al., "Structure-Activity Relationship and Classification of Flavonoids as Inhibitors of Xanthine Oxidase and Superoxide Scavengers," J. Nat. Prod., (1998), 61:71-76.
Database CA Chemical Abstract Service, Li et al., "Substituted-benzoheterocycle derivatives, preparation, and application for preparation of antiviral or antineoplastic drugs," XP002726578 retrieved from STN Database accession No. 2013:366779 (abstract); RN:1427163-92-5 & CN 102 952 062 A, Mar. 6, 2013, 2 pages.
Database Pubchem Compound Dec. 4, 2011 XP 003033770 (11 pages).
Database Registry, 2011, RN 1289869-72-2, 1027970-95-1, 959671-57-9.
Database Registry, 2012, RN 1390863-18-9, 1390573-58-6, 1389652-57-6, 1387166-17-7, 1318517-26-8, 1318395-05-9, 933829-46-0, 879919-21-8.
Davidovich, et al. Detection of polymorphism by powder x-ray diffraction: interference by preferred orientation. Am. Pharm. Rev. 2004; 10, 12, 14, 16, 100.
Dean. Analytical Chemistry Handbook. University of Tennesse, Knoxville. McGraw-Hill, Inc. 1995; 10.24-10.26.
Deem. "Red Blood Cells and Hemoglobin in Hypoxic Pulmonary Vasoconstriction" Advances in experimental medicine and biology, (2006) 588, 217-231.
Desai et al. Preparation of N-[ro-(4-aryl-1-piperazinyl)ethyl/propyl]-3-hydroxyphthalimidines. Indian Journal of Chemistry. 39:455-457 (2000).
Desideri et al., "Guanylhydrazones of 3-substituted 2-pyridinecarboxaldehyde and of (2-substituted 3-pyridinyloxy) acetaldehyde as prostanoid biosynthesis and platelet aggregation inhibitors", European Journal of Medicinal Chemistry, Editions Scientifique Elsevier, Paris, FR, 1991, vol. 26, No. 4, pp. 455-460.
Di Stilo, et al. New 1,4-dihydropyridines conjugated to furoxanyl moieties, endowed with both nitric oxide-like and calcium channel antagonist vasodilator activities. J. Med. Chem. 41:5393-5401 (1998).
Ding et al., "Crystal structure of bis[µ2-2-(2-formylphenoxy)acetato-O,O]-bis[µ2-2-2-formylphynoxy)acetato-O,O]- octakis(n-butyl)tetratin(IV), Sn4O2(C9H7O4)4(C4H9)8", Zeitschrift fuer Kristallographie—New Crystal Structures (2011), 226(1), 31-32 CODEN:ZKNSFT; ISSN: 1433-7266.
Doelker, English translation of S.T.P, Pratiques (1999), 9(5), 399-409.
Doelker. English translation of Ann. Pharm. Fr., 2002, 60: 161-176.
Einfalt, et al. Methods of amorphization and investigation of the amorphous state. Acta Pharm. 2013; 63:305-334.
Elwahy, "Synthesis of new benzo-substituted macrocyclic containing quinoxaline subunits" Tetrahedron (2000), 56(6), 897-907 CODEN:TETRAB; ISSN:0040-4020.
Epsztajn et al., "Application of organolithium", Tetrahedron, Elsevier Science Publishers, Amsterdam, NL, 1991, vol. 47, No. 9, pp. 1697-1706.
European Search Report and Search Opinion dated Aug. 4, 2015 for EP Application No. 12862525.8. 9 pages.
European Search Report and Search Opinion dated Jul. 21, 2016 for EP Application No. 14769616.5. 8 pages.
European Search Report and Search Opinion dated May 28, 2015 for EP Application No. 12862096.0. 13 pages.
European Search Report and Search Opinion dated Nov. 16, 2016 for EP Application No. 16194019.2. 13 pages.
European Search Report and Search Opinion dated Sep. 26, 2016 for EP Application No. 14768759.4. 6 pages.
Extended European Search Report and opinion dated Jul. 20, 2016 for EP Application No. 14768414.6. 10 pages.
Extended European Search Report and Search Opinion dated Jul. 18, 2016 for EP Application No. 14770695.6. 13 pages.

(56) References Cited

OTHER PUBLICATIONS

Extended European Search Report and Search Opinion dated Jul. 7, 2016 for EP Application No. 14768317.1. 7 pages.
Extended European Search Report and Search Opinion dated May 17, 2017 for EP Application No. 15746995.8. 8 pages.
Extended European Search Report and Search Opinion dated Nov. 23, 2015 for EP Application No. 12862525.8. 16 pages.
Gadaginamath, et al., "Synthesis and antibacterial activity of novel 1-butyl-2-phenoxyl2-phenylthlol2-aminomethyl-5- methoxyindole derivatives", Polish Journal of Chemistry (1997), 71(7), 923-928 CODEN: PJCHDQ; ISSN:0137-5083.
Gao et al, "A novel one-pot three-step synthesis of 2-(1-benzofuran-2-yl)quinoline-3-carboxylic acid derivatives", Journal of the Brazilian Chemical Society (2010), 21(5). 806-812 CODEN:JOCSET; ISSN: 0103-5053.
Ghate et al., "Synthesis of vanillin ethers from 4-(bromomethyl) coumarins as anti-inflammatory agents,"European Journal of Medicinal Chemistry (2003), 38(3), 297-302 CODEN: EJMCA5; ISSN: 0223-5234.
Gibson et al., "Novel small molecule bradykinin B2 receptor antagonists", Journal of Medicinal Chemistry, 2009, vol. 52, pp. 4370-4379.
Glasson et al. Metal Template Synthesis of a Tripodal Tris(bipyridyl) Receptor that Encapsulates a Proton and an Iron (ii) Centre in a Pseudo Cage. Aust. J. Chem. 65:1371-1376 (2012).
Grashey, "The nitro group as a 1,3-dipole in cycloadditions" Angewandte Chemie (1962), 74, 155 CODEN: ANCEAD; ISSN: 0044-8249.
Guillaumel, et al. Synthetic routes to 2-(2-benzofuranyl)benzoic acids and their cyclization into benz[6]indeno[2,1-d]furan-10-ones. Journal of Heterocyclic Chemistry, 1990; 27: 1047-1051. doi:10.1002/jhet.5570270444.
Guillory (in Brittain ed.) Polymorphism in Pharmaceutical Solids. NY, Marcel Dekker, Inc. 1999; 1-2:183-226.
Gunter et al., "Structural control of co-receptor binding in porphyrin-bipyridinium supramolecular assemblies", Journal of the Chemical Society, Perkin Transactions 1: Organic and Bio-Organic Chemistry (1998), (12), 1945-1958 CODEN: JCPRB4; ISSN: 0300-922X.
Hang, Song. "Pharmaceutical Separation Engineering" East China University of Technology Press. Aug. 31, 2011; 270-272. (in Chinese with English abstract).
Hanmantgad et al., "Synthesis and pharmacological properties of some r-(2-benzo[b]furanyl)coumarins" Indian Journal of Chemistry, Section B: Organic Chemistry Including Medicinal Chemistry (1986), 25B(7), 779-81 CODEN: IJSBDB; ISSN: 0376-4699.
He et al., "Prodrugs of Phosphonates, Phosphinates, and Phosphates", Prodrugs: Challenges and rewards Part 2, edited by Stella et al., 2007, pp. 223-264.
Heimbach et al., "Enzyme-mediated precipitation of patent drugs from their phosphate prodrugs", International Journal of Pharmaceutics, 261, p. 81-92, 2003.
Heimbach et al., "Prodrugs: Challenges and Rewards Part I," New York, NY, Singer:AAPS Press, (2007), 5(Chapter 2.2.1):157-215 Overcoming Poor Aqueous Solubility of Drugs for Oral Delivery.
Heimgartner et al., "Stereoselective synthesis of swainsonines from pyridines", Tetrahedron, Elsevier Science Publishers, Amsterdam, NL, 2005, vol. 61, No. 3, pp. 643-655.
Hoffman, et al. 3-Hydroxy-3-methyglutaryl-coenzyme A Reductase Inhibitors, 2. Structural Modification of 7-(Substituted aryl)-3,5-dihydroxy-6-heptenoic Acids and Their Lactone Derivatives. Journal of Medical Chemistry. 29(2):159-169 (1986).
Hong et al., "Potential Anticancer Agents VI: 5-Substituted Pyrimidine-6-Carboxaldehydes", Journal of Pharmaceutical Sciences, American Pharmaceutical Association, Washington, US, 1970, vol. 59, No. 11, pp. 1637-1645.
Huckauf, et al., "Oxygen Affinity of Haemoglobin and Red Cell Acid-Base Status in Patients with Severe Chronic Obstructive Lung Disease" Bull. Europe Physiopath. Resp., 1976, 12, 129-142.
International Preliminary Report on Patentability for PCT/US2014/022846 dated Sep. 15, 2015. 7 pages.
International Preliminary Report on Patentability for PCT/US2014/022742 dated Sep. 15, 2015. 7 pages.
International Preliminary Report on Patentability for PCT/US2014/022733 dated Sep. 15, 2015. 11 pages.
International Preliminary Report on Patentability for PCT/US2014/022769 dated Sep. 15, 2015. 8 pages.
International Search Report and Written Opinion dated Aug. 19, 2014 for PCT Application No. PCT/US2014/022736. 14 pages.
International Search Report and Written Opinion dated Aug. 27, 2014 for PCT Application No. PCT/US2014/022742. 11 pages.
International Search Report and Written Opinion dated Aug. 4, 2017 for PCT Application No. PCT/US2017/032104. 10 pages.
International Search Report and Written Opinion dated Dec. 8, 2014 for PCT Application No. PCT/US2014/052575. 10 pages.
International Search Report and Written Opinion dated Jan. 22, 2018 for PCT Application No. PCT/US2017/056352. 12 pages.
International Search Report and Written Opinion dated Jul. 22, 2014 for PCT Application No. PCT/US2014/022846. 11 pages.
International Search Report and Written Opinion dated Jul. 30, 2014 for PCT Application No. PCT/US2014/029682. 16 pages.
International Search Report and Written Opinion dated Jul. 31, 2014 for PCT Application No. PCT/US2014/022789. 13 pages.
International Search Report and Written Opinion dated Jul. 4, 2014 for PCT Application No. PCT/US2014/022769. 11 pages.
International Search Report and Written Opinion dated Mar. 5, 2013 for PCT Application No. PCT/US2012/072177. 7 pages.
International Search Report and Written Opinion dated May 11, 2015 for PCT Application No. PCT/US2015/014589. 5 pages.
International Search Report and Written Opinion dated May 20, 2013 for PCT Application No. PCT/US2012/072183. 11 pages.
International Search Report and Written Opinion dated Nov. 28, 2014 for PCT Application No. PCT/US2014/052576. 10 pages.
International Search Report and Written Opinion dated Oct. 31, 2014 for PCT Application No. PCT/US2014/013575. 10 pages.
Israel office action dated Aug. 11, 2016 for Israeli Patent Application No. 233329.
Ito et al., A medium-term rat liver bioassay for rapid in vivo detection of carcinogenic potential of chemicals,01D Cancer Science, Jan. 2003, 94, pp. 3-8.
Ivanisevic, et al. Uses of x-ray powder diffraction in the pharmaceutical industry. Pharm. Sci. Encycl. 2010; 1-42.
Jain, et al., "Polymorphism in Pharmacy", Indian Drugs, 1986, 23(6) 315-329.
Jarvest et al., "Discovery and optimisation of potent, selective, ethanolamine Inhibitors of bacterial phenylalanyl tRNA synthetase", Bioorganic & Medicinal Chemistry Letter (2005), 15(9), 2305-2309 CODEN: BMCLES; ISSN: 0960-894X.
Karche et al., "Electronic Effects in Migratory Groups [1,4]- versus [1,2]- Rearrangement in Rhodium Carbenoid Generated Bicyclic Oxonium Ylides", Journal of Organic Chemistry (2001), 66(19), 6323-6332 CODEN: JOCEAH; ISSN: 0022-3263.
Katritzky et al., "Syntheses of 3-hydroxymethyl-2-3-dihydrobenzofurans and 3-hydroxymethylbenzofurans", ARKIVOC (Gainesville, FL, United States) (2003), (6), 49-61 CODEN: AGFUAR URL: http://www.arkat-usa.org/ark/journal/2003/Vargoglis/AV-622A/6ss.pdf.
Kaye et al., "DABCO-catalyzed reactions of salicylaldehydes with acrylate derivatives", Synthetic Communications (1996), 26(11), 2085-97 CODEN: SYNCAV; ISSN: 0039-7911.
Kaye et al., "Does the DABCO-catalyzed reaction of 2-hydroxybenzaldehydes with methyl acrylate follow a Baylis-Hillman pathway?", Organic & Biomolecular Chemistry (2003), 1(7), 1133-1138 CODEN: OBCRAK; ISSN: 1477-0520.
Keidan, et al. Effect of BW12C on oxygen affinity of hemoglobin in sickle-cell disease. The Lancet. 1986; 327(8485):831-834.
Kessar et al., "Synthesis of Isoindolobenzazepines via photocyclisation of N-(2-formylphenethyl)phthalimide derivatives", Indian Journal of Chemistry, Section B: Organic Chemistry Including Medicinal Chemistry (1991), 30B(11), 999-1005 CODEN: JSBDB; ISSN:3076-4699.
Kessar et al., An Interesting Application of Photocyclisation in Apophdeadane Alkaloid Synthesis. Tetrahedron Letters (1987), 28(44), 5323-5326. CODEN: TELEAY; ISSN: 0040-4039.

(56) References Cited

OTHER PUBLICATIONS

Kirk-Othmer Encyclopedia of Chemical Technology. 2002; 8:95-147.
Kise et al., "Electroreductive Intramolecular Coupling of Phthalimides with Aromatic Aldehydes: Application to the Synthesis of Lennoxamine". Journal of Organic Chemistry (2011), 76(23), 9856-9880 CODEN:JOCEAH; ISSN: 0022-3263.
Klis, et al. Halogen-lithium exchange versus deprotonation: synthesis of diboronic acids derived from aryl-benzyl ethers. Tetrahedron Letters, 48(7):1169-1173 (2007).
Kratochvil. Chapter 8 Solid Forms of Pharmaceutical Molecules. J. Sestak et al. (eds.), Glassy, Amorphous and Nano-Crystalline Materials. Hot Topics in Thermal Analysis and Calorimetry 8, 2011, pp. 129-140.
Kraus, et al. Michael additions in anhydrous media. A novel synthesis of oxygenated coumarins. J. Org. Chem., 1979, 44 (14), pp. 2480-2482.
Krow,"The Baeyer-Villiger oxidation of ketones and aldehydes", Organic Reactions (Hoboken, NJ, United States) (1993), 43, No pp. given CODEN: ORHNBA URL: http://www3.interscience.wiley.com/cgi-bin/mrwhome/107610747/HOME.
Kucera, et al. Evaluation of Ceolus(TM) microcrystalline cellulose grades for the direct compression of enteric-coated pellets. Drug Development and Industrial Pharmacy. Mar. 1, 2012; 38(3):341-350.
Lakkannavar et al., "4-[2'-benzylideneanlino aryloxymethyl] coumarins E and Z isomers". Indian Journal of Heterocyclic Chemistry (1995), 4(4), 303-4 CODEN: IJCHEI; ISSN: 0971-1627.
Lin et al. Synthesis and anticancer activity of benzyloxybenzaldehyde derivatives against HL-60 cells. Bioorganic & Medicinal Chemistry. 13(5), 1537-1544 (2005).
Lin et al., "Potential Antitumor Agents.8. Derivatives of 3- and 5-Benzyloxy-2-formylpyridine Thiosemicarbazone", Journal of Medicinal Chemistry, American Chemical Society, US, 1972, vol. 15, No. 6, pp. 615-618.
Liu et al., "Synthesis of Double-Armed Benzo- 15-crown-5 and Their Complexation Thermodynamics with Alkali Cations", Journal of Inclusion Phenomena and Macrocyclic Chemistry (2005), 52(3-4), 229-235 CODEN: JIPCF5; ISSN: 1388-3127.
Luan, et al. TOPS-MODE model of multiplexing neuroprotective effects of drugs and experimental-theoretic study of new 1,3-rasagiline derivatives potentially useful in neurodegenerative diseases. Bioorganic & Medicinal Chemistry. 2013; 21:1870-1879.
Mahoney et al., "Functionalization of Csp3-H bond-Sc(OTf)3-catalyzed domino 1,5-hydride shift/cyclization/Friedel-Crafts acylation reaction of benzylidene Meldrum's acids", Tetrahedron Letters (2009), 50(33), 4706-4709 CODEN: TELEAY; ISSN: 0040-4039.
Majhi et al., "An efficient synthesis of novel dibenzo-fused nine-membered oxacycles using a sequential Baylis-Hillman reaction and radical cyclization", Synthesis (2008), (1), 94-100 CODEN: SYNTBF; ISSN: 0039-7881.
Manna et al., Synthesis and beta-adrenoreceptor blocking activity of [[3-(alkylamine)-2-hydroxypropyl]oximino]pyridines and 0[3-(alkylamine)-2-hydroxypropyl]methylpyridine ketone oximes derivatives, Il Farmaco, 1996, vol. 51, No. 8, 9, pp. 579-587.
Mantyla et al., Synthesis, in vitro evaluation, and antileishmanial activity of water-soluble prodrugs of buparvaquone. J. Med. Chem. 2004, 47:188-195.
Marchetti et al., "Synthesis and biological evaluation of 5-substituted O4-alkylpyrimidines as CDK2 inhibitors," Org. Biomol. Chem, 2010, vol. 8, pp. 2397-2407.
"Master of Engineering Education Chemical Engineering Development Report" National Engineering Education Master in Chemical Engineering Cooperation Group, Zhejiang University Press. Mar. 31, 2011; 241-245. (in Chinese with English abstract).
Mathur. "Microcrystalline Cellulose" In: "Handbook of Pharmaceutical Excipients, Second Edition", Jan. 1, 1994, The Pharmaceutical Press, London, pp. 84-87.
McKay et al., 7,11,15,28- Tetrakis[(2-formylphenoxy)methyl]-1,21,23,25- tetramethylresorcin[4]arene cavitand ethyl acetate clathrate at 173 K, Acta Crystallographica, Section E: Structure Reports Online (2009), E65(4), 692-693 CODEN: ACSEBH; ISSN: 1600-5368 URL: http://journals.lucr.org/e/issues/2009/04/00fl22 33/fl2233.pdf.
McKay et al., "Microwave-assisted synthesis of a new series of resorcin[4]arene cavitand-capped porphyrin capsules", Organic & Biomolecular Chemistry (2009), 7(19), 3958-3968 CODEN: OBCRAK; ISSN: 1477-0520.
Merlino et al., "Development of second generation amidinohydrazones, thio- and semicarbazones as Trypanosoma cruzi-inhibitors bearing benzofuroxan and benzimidazole 1,3-dioxide core scaffolds", MedChemComm (2010), 1(3), 216-228 CODEN: MCCEAY; ISSN: 2040-2503.
Mesguiche et al.,"4-Alkoxy-2,6-diaminopyrimidine Derivatives: Inhibitors of Cyclin Dependent Kinases 1 and 2," Bioorganic & Medicinal Chemistry Letters, Jan. 2003, vol. 13, pp. 217-222.
Metcalf, et al., "Discovery of GBT440, an Orally Bioavailable R-State Stabilizer of Sickle Cell Hemoglobin," ACS Med. Chem. Lett., 2017, 8, 321-326.
Mitra et al., "Synthesis and biological evaluation of dibenz[b,f][1,5]oxazocine derivatives for agonist activity at x-opioid receptor", European Journal of Medicinal Chemistry (2011), 46(5), 1713-1720 CODEN: EJMCA5; ISSN: 0223-5234.
Mulwad et al., "Synthesis and antimicrobial activity of [6'-methyl-4'-methoxy-2-oxo-2H-[1]-benzopyran)-2",4" dihydro-[1",2",4"}-triazol-3' -one and 3'phenylthiazolidin-4' -one-phenoxymethyl derivatives of dipyranoquinoline", Pharmaceutical Chemistry Journal Ahead of Print CODEN: PCJOAU; ISSN: 0091-150, 2011; pp. 427-432.
Muzaffar, et al., "Polymorphism and Drug Availability: a Review" J of Pharm. (Lahore), 1979, 1(1), 59-66.
Nagy et al., Selective coupling of methotrexate to peptide hormone carriers through a y-carboxamide linkage of its glutamic acid moiety: Benzotriazol-1-yloxytris(dimethylamino)phosphonium hexafluorophosphate activation in salt coupling. Proc. Natl. Acad. Sci. USA 1993, 90:6373-6376.
Neelima et al., "A novel annelation reaction: synthesis of 6H-[1]benzopyrano[4,3-b]quinolines "Chemistry & Industry (London, United Kingdom) (1986), (4), 141-2 CODEN: CHINAG; ISSN: 0009-3068.
Nnamani, et al., "Pyridyl derivatives of benzaldehyde as potential antisickling agents," Chem. Biodivers., (2008), 5(9):1762-1769.
Nogrady, Medicinal Chemistry A Biochemical Approach, Oxford University Press, New York, pp. 388-393 (1985).
Nonoyama et al.,"Cyclometallation of 2-(2-pyridyl)benzo[b]furen and 1-(2-pyridyl and 2-pyrimidyl)indole with palladium(II) and rhodium(III). Structures of unexpectedly formed nitro palladium(II) complexes", Polyhedron 1999, 533-543 CODEN: PLYHDE; ISSN: 0277-5387.
Notice of Allowance dated Dec. 19, 2014 for U.S. Appl. No. 13/730,730. 11 pages.
Nyerges et al, "Synthesis of Indazole N-oxides via the 1,7-electrocyclization of azomethine ylides", Tetrahedron Letters (2001), 42(30), 5081-5083 CODEN: TELEAY; ISSN:0040-4039.
Nyerges et al, "Synthesis of Indazole N-oxides via the 1,7-electrocyclization of azomethine ylides", Tetrahedron Letters (2004), 60(44), 9937-9944 CODEN: TETRAB; ISSN:0040-4020.
OECD SIDS "SIDS Initial Assessment Report for 13th SIAM," Nov. 2001, pp. 1-95.
Office Action dated Aug. 29, 2014 for U.S. Appl. No. 13/730,730. 17 pages.
Office Action dated Dec. 3, 2013 for U.S. Appl. No. 13/730,674. 8 pages.
Office Action dated Jul. 6, 2015 for U.S. Appl. No. 13/815,874. 14 pages.
Office Action dated Jun. 12, 2015 for CN Application No. 201280070743.5. 13 pages.
Office Action dated Jun. 29, 2015 for U.S. Appl. No. 13/815,810. 19 pages.
Office Action dated Jun. 30, 2014 for U.S. Appl. No. 13/730,674. 9 pages.
Office Action dated Sep. 18, 2013 for U.S. Appl. No. 13/730,674. 10 pages.

(56) References Cited

OTHER PUBLICATIONS

Oh, et al. Solid-phase synthesis of 1,3-oxazolidine derivatives. Tetrahedron Letters. 2000; 41:5069-5072.
O'Reilly, "Metal-phenoxyalkanoic acid interactions, XXV. The crystal structures of (2-formyl-6-methoxyphenoxy)acetic acid and its zinc(II)complex and the lithium, zinc(II) and cadmium(II) complexes of (2-chlorophenoxy)acetic acid", Australian Journal of Chemistry (1987), 40(7)m 1146-59 CODEN; AJCHAS; ISSN:0004-9425.
Otsuka, et al., "Effect of Polymorphic Forms of Bulk Powders on Pharmaceutical Properties of Carbamazepine Granules." Chem. Pharm. Bull., 47(6) 852-856 (1999).
Patani, et al. Bioisosterism: A Rational Approach in Drug Design. J. Chem Rev. 1996, 96(8), pp. 3147-3176.
Pearson, et al. Experimental and Computational Studies into an ATPH-Promoted exo-Selective IMDA Reaction: A Short Total Synthesis of Δ9-THC*. Chem. Eur. J. 2010, 16, 8280-8284.
Perez et al., "Preparation of new 1,2-disubstituted ferrocenyl ammonium salt", Polyhedron (2009), 28(14), 3115-3119 CODEN: PLYHE; ISSN:0277-5387.
Perkins et al., "Manganese(II), Iron(II), cobalt(II), and cooper(II)complexes of an extended inherently chiral tris-bipyridyl cage", Proceedings of the National Academy of Sciences of the United States of America (2006), 103(3), 532-537 CODEN: PNASA6; ISSN: 0027-8424.
Potapov, et al. A convenient synthesis of heterocyclic compounds containing 11-oxo-6,11,12,13-tetrahydrodibenzo[b,g][1,5]oxazonine fragment. Mendeleev Communications. 2009; 19:287-289.
Prohens, et al. Polymorphism in pharmaceutical industry. The Pharmacist. Apr. 1, 2007; 373:58-68. (in Spanish with English abstract).
PUBCHEM CID 54009805 Create Date: Dec. 4, 2011 p. 1.
PUBCHEM CID 54883281 Create Date: Aug 19, 2012 p. 1.
Remington's Pharmaceutical Sciences, 17th Edition, A. Gennaro editor, Easton Pennsylvania. Table of Contents. (1985).
Rodriguez-Spong, et al. General principles of pharmaceutical solid polymorphism: a supramolecular perspective. Adv Drug Deliv Rev. Feb. 23, 2004;56(3):241-74.
Rolan et al., "The pharmacokinetics, tolerability and pharmacodynamics of tucaresol (589C80); 4[2- formyl-3-hydroxyphenoxymethyl] benzoic acid), a potential anti-sickling agent, following oral administration to healthy subjects", British Journal of Clinical Pharmacology, 1993, 35(4):419-425.
Rooseboom et al., Enzyme-catalyzed activation of anticancer prodrugs. Pharmacol. Rev. 2004, 56:53-102.
Ruchirawat et al., "A novel synthesis of aporhoeadanes", Tetrahedron Letters (1984), 25(32), 3485-8 CODEN: TELEAY; ISSN: 0040-4039.
Safo, et al. Structural basis for the potent antisickling effect of a novel class of five-membered heterocyclic aldehydic compounds. J Med Chem. Sep. 9, 2004;47(19):4665-76.
Sahakitpichan et al., "A practical and highly efficient synthesis of lennoxamine and related isoindoloenzazepines" Tetrahedron (2004), 60(19), 4169-4172 CODEN: TETRAB; ISSN: 0040-4020.
Sahm et al., "Synthesis of 2-arylbenzofurans" Justus Liebigs Annalen der Chemie (1974), (4), 523-38 CODEN: JLACBF; ISSN: 0075-4617.
Sainsbury et al., "1,2-Dihydroisoquinolines, IV. Acylation" Tetrahedron (1966), 22(8), 2445-52 CODEN: TETRAB; ISSN: 0040-4020.
Sarodnick et al., "Quinoxalines XV, Convenient Synthesis and Structural Study of Pyrazolo[1,5-a]quinoxalines", Journal of Organic Chemistry (2009), 74(3), 1282-1287 CODEN: JOCEAH; ISSN: 0022-3263.
Schudel, et al. Uber die Chemie des Vitamins E. Helvetica Chimica Acta. 1963; 66:636-649.
Seddon. Pseudopolymorph: A Polemic. The QUILL Centre, The Queen's University of Belfast, United Kingdom. Jul. 26, 2004. 2 pages.

Shetty et al. Palladium catalyzed alpha-arylation of methyl isobutyrate and isobutyronitrile: an efficient synthesis of 2,5-disubstituted benzyl alcohol and amine intermediates. Tetrahedron Letters, 47:8021-8024 (2006).
Siddiqui et al., "The Presence of Substitutents on the Aryl Moiety of the Aryl Phosphoramidate Derivative of d4T Enhances Anti-HIV Efficacy in Cell Culture-Activity Relationship," J. Med. Chem., (1999), 42:393-399.
Silva et al., "Advances in prodrug design," Mini Rev. Med. Chem., (2005), 5(10):893-914.
Singh et al., "Reductive-Cyclization-Mediated Synthesis of Fused Polycyclic Quinolines from Baylis-Hillman Adducts of Acrylonitrile: Scope and Limitations", European Journal of Organic Chemistry (2009), (20), 3454-3466 CODEN: EJOCFK; ISSN:1434-193X.
Singhal, et al., "Drug Polymorphism and Dosage Form Design: a Practical Perspective" Advanced Drug Delivery reviews 56, p. 335-347 (2004).
Sobolev et al., Effect of acyl chain length and branching on the enantioselectivity of Candida rugosa lipase in the kinetic resolution of 4-(2-difluoromethoxyphenyl)-substituted 1,4-dihydropyridine 3,5-diesters. J. Org. Chem. 2002, 67:401-410.
Srivastava et al., "Synthesis and biological evaluation of 4-substituted tetrazolo[4,5-a]quinolines and 2,3-disubstituted quinoline derivatives", Indian Journal of Chemistry, Section B: Organic Chemistry Including Medicinal Chemistry (1989), 28B(7), 562-73 CODEN: IJSBOB; ISSN:0376-4699.
Starke et al., "Quinoxalines, Part 13: Synthesis and mass spectrometric study of aryloxymethylquinoxalines and benzo[b]furylquinoxalines" Tetrahedron (2004), 60(29), 6063-6078 CODEN: TETRAB; ISSN:0040-4020.
Stetinova, et al. Synthesis and Properties of 4-Alkylaminomethyl and 4-Alkoxymethyl Derivatives of 5-Methyl-2-Furancarboxylic Acid. Collection Czechosloval Chem. Commun. 1985; 51:2186-2192.
STN Registry Database Entry: CAS RN 1039927-57-5 (Entered STN: Aug. 20, 2008).
STN Registry Database Entry: CAS RN 1243541-58-3 (Entered STN: Sep. 29, 2010).
Strickley. Solubilizing excipients in oral and injectable formulations. Pharm Res. Feb. 2004;21(2):201-30.
Swann et al., "Rates of reductive elimination of substituted nitrophenols from the (indol-3-yl)methyl position of indolequinones", Journal of the Chemical Society, Perkin Transactions 2 (2001), (8), 1340-1345.
Table of Compounds, each of which can be found either in Table 1 of U.S. Pat. No. 9,018,210 or Table 1 of U.S. Pat. No. 9,012,450.
Taday, et al., "Using Terahertz Pulse Spectroscopy to Study the Crystalline Structure of a Drug: A Case Study of the Polymorphs of Ranitidine Hydrochloride." J of Pharm. Sci., 92(4), 2003, 831-838.
Testa et al., Hydrolysis in Drug and Prodrug Metabolism, Jun. 2003, Wiley- VCH, Zurich, 419-534.
Tome et al., "Product class 13: 1,2,3-triazoles", Science of Synthesis (2004), 13, 415-601 CODEN: SSCYJ9.
Tsuge, et al. Suppressive Effect of Vitamin B6-Sugar Derivatives on The Proliferation of Feline Mammary Tumor Cell, FRM. Vitamins (Japan), 2006; 80(11):537-542. (In Japanese with English Abstract).
U.S. Pharmacopia #23, National Formulary #18, 1995, 1843-1844.
Van Halbeek, et al., "Sialic Acid in Permethylation Analysis: Prepared and Identification of Partially O-Methylated Derivatives of methyl N-Acetyl-N-Methyl-beta-D-Neurominate Methyl Glycoside", Carbohydrate Research, vol. 60, No. 1, 1978, pp. 51-62, 53, and 59.
vanRompaey et al., "A versatile synthesis of 2-substituted 4-amino-1,2,4,5-tetrahydro-2-benzazepine-3-ones", Tetrahedron (2003), 59(24), 4421-4432 CODEN: TETRAB; ISSN:0040-4020.
vanRompaey et al., "Synthesis and evaluation of the 3B2-turn properties of 4-amino-1,2,4,5-tetrahydro-2-benzazepin-3-ones and of their spirocyclic derivative", European Journal of Organic Chemistry (2006), (13), 2899-2911 CODEN: EJOCFK; ISSN: 1434-193X.
Vicente et al., "Carbopalladation of Maleate and Fumarate Esters and 1,1-Dimethylallene with Ortho-Substituted Aryl Palladium Complexes" Organometallics (2010), 29(2), 409-416.

(56) References Cited

OTHER PUBLICATIONS

Vichinsky. "Emerging 'A' therapies in hemoglobinopathies: agonists, antagonists, antioxidants, and arginine." Hematology 2012, 271-275.
Vippagunta, et al. Crystalline Solids. Advanced Drug Delivery Reviews. 2001; 48:3-26.
Wang et al., "Studies of Benzothiophene Template as Potent Factor IXa (FIXa) Inhibitors in Thrombosis", Journal of Medicinal Chemistry (2010), 53, 1465-1472.
Warshawsky et al., "The synthesis of aminobenzazespinones as anti-phenylalanine dipeptide mimics and their use in NEP inhibition", Bioorganic & Medicinal Chemistry Letter (1996), 6(8), 957-962 CODEN: BMCLE8; ISSN: 0960-894X.
Wendt et al., "Synthesis and SAR of 2-aryl pyrido[2,3-d]pyrimidines as potent mGlu5 receptor antagonists", Bioorganic & Medicinal Chemistry Letters, Pergamon, Amsterdam, NL, vol. 17, No. 19, Sep. 14, 2007 (Sep. 14, 2007), pp. 5396-5399.
Wermuth, Camille G., "Molecular Variations Based on Isosteric Replacements", The Practice of Medicinal Chemistry, 1996, pp. 203-232.
Yan et al., "Synthesis, crystal structure and antibacterial activity of dibutyltin carboxylate", Huaxue Tongbao (2007), 70(4), 313-316 CODEN: HHTPAU; ISSN: 0441-3776.
Yan et al., "Synthesis, crystal structure and antibacterial activity of di-n-butyltin di-2(2-formylphenoxy)acetic ester", Yingyong Huaxue (2007), 24(6), 660-664.
Yang, et al. Structural requirement of chalcones for the inhibitory activity of interleukin-5. Bioorg Med Chem. Jan. 1, 2007;15(1):104-11. Epub Oct. 10, 2006.
Yoon et al., The Chirality Conversion Reagent for Amino Acids Based on Salicyl Aldehyde. Bull. Korean Chem. Soc., (2012), 33:1715-1718.
Zhang et al., "DFT study on Ru11-catalyzed cyclization of terminal alkynals to cycloalkenes", International Journal of Quantum Chemistry (2009), 109(4), 679-687 CODEN: IJQCB2; ISSN:0020-7608.
Zhang, et al. A selective fluorescent chemosensor with 1, 2, 4-triazole as subunit for Cu (II) and its application in imaging Cu (II) in living cells. Dyes and Pigments. 2012; 92(3):1370-1375.
Zhang, et al. Current prodrug strategies for improving oral absorption of nucleoside analogues. Asian Journal of Pharmaceutical Sciences. Apr. 2014; 9(2):65-74.
Zhu et al., "Isoquinoline-pyridine-based protein kinase B/Akt antagonists: SAR and in vivo antitumor activity", Bioorganic & Medicinal Chemistry Letters, Pergamon, Amsterdam, NL, 2006, vol. 16, No. 12, pp. 3150-3155.
Zwaagstra et al., "Synthesis and Structure-Activity Relationships of Carboxylated Chalcones: A Novel Series of Cys-LT1 (LTD4) Receptor Antagonists", Journal of Medicinal Chemistry (1997), 40(7), 1075-1089 CODEN: JMCMAR; ISSN: 0022-2623.
Byrn, et al. Pharmaceutical solids: a strategic approach to regulatory considerations. Pharmaceutical Research. 1995; 12(7):945-954.
Goodman and Gilman's The Pharmacological Basis of Therapeutics (Tenth Edition 2001), McGraw Hill. Chapter I, pp. 3-29.
Paul, et al. Hydroxyl directed C-arylation: synthesis of 3-hydroxyflavones and 2-phenyl-3-hydroxy pyran-4-ones under transition-metal free conditions. Org. Biomol. Chem., 2018, 16:444-451.
Ashizawa et al., Polymorphism and crystallization of the pharmaceutical drugs (Iyakuhin No Takeigensho to Shoseki No Kagaku) Maruzen Planet Co., Ltd., Sep. 20, 2002, pp. 3-16 and pp. 273-278. (in Japanese with partial English translation).
Beringer et al., Remington's Pharmaceutical Sciences, Mack Pub., 21st Edition, 2005, pp. 1072-1076.
"Can Voxelotor Offer New Hope for Sickle Cell Disease?," Dec. 3, 2018, available at: https://www.ashclinicalnews.org/on-location/voxelotor-offers-new-hope-sickle-cell-disease/. 4 pages.
Experimental Chemistry (vol. 2)(Jikken Kagaku Koza, Zoku), Separation and refining, Maruzen Co.Ltd. Jan. 25, 1967, pp. 159-178 and pp. 186-187. (in Japanese with partial English translation).
GBT Announces Positive Top-line Data from Part A of the Phase 3 HOPE Study of Voxelotor in Sickle Cell Disease, Press Release dated Jun. 27, 2018. Available at http://ir.gbt.com/phoenix.zhtml?c=254105&p=irol-newsArticle&ID=2356168.
Gu, et al. Grouping solvents by statistical analysis of solvent property parameters: implication to polymorph screening. Int J Pharm. Sep. 28, 2004;283(1-2):117-25.
International Preliminary Report on Patentability dated Jun. 5, 2018 for PCT/US2016/064723. (10 pages).
International Search Report and Written Opinion dated May 3, 2017 for PCT Application No. PCT/US2016/064723. 15 pages.
Lehrer, et al. GBT440, a novel anti-polymerization agent, for the treatment of sickle cell disease. Global Blood Therapeutics. Apr. 1, 2016. (50 pages) Retrieved from the Internet: http://casicklecell.org/img/PresentationSlidesWebinar3.pdf.
New Introduction of Pharmacology (Sin Yakuzaigaku Soron)(revised 3rd Edition),Apr. 10, 1987, Nankodo Co., Ltd p. 111. (in Japanese with partial English translation).
New Pharmaceutical Preparation (Shin Seizaigaku), Nanzando Co.,Ltd., Apr. 25, 1984, p. 102-103 and pp. 232-233. (in Japanese with partial English translation).
Pharmacy -Foundation and Application-(Chozaigaku, Kiso to Ouyou), Nanzando Co.,Ltd., Sep. 20, 1977 p. 142-145. (in Japanese with partial English translation).
Reagan-Shaw, et al. Dose translation from animal to human studies revisited. The FASEB Journal. Mar. 2007; 22:659-661.
Shin, et al. Interpretation of Animal Dose and Human Equivalent Dose for Drug Development. The Journal of Korean Oriental Medicine. 2010; 31(3):1-7.
The Pharmacopoeia of Japan the Sixteen edition, 2011 pp. 64-68 2.58 X-ray powder diffraction measuring method p. 2070 (in Japanese with partial English translation).

PROCESS FOR SYNTHESIZING 2-HYDROXY-6-((2-(1-ISOPROPYL-1H-PYRAZOL-5-YL)-PYRIDIN-3-YL)METHOXY) BENZALDEHYDE

CROSS-REFERENCE TO RELATED APPLICATIONS

This application is a continuation of U.S. patent application Ser. No. 15/593,198, filed May 11, 2017, now U.S. Pat. No. 10,077,249, which application claims priority to U.S. Provisional Patent Application No. 62/335,583, filed May 12, 2016, each of which is incorporated herein by reference in its entirety and for all purposes.

FIELD

Disclosed herein are processes for synthesizing 2-hydroxy-6-((2-(1-isopropyl-1H-pyrazol-5-yl)-pyridin-3-yl)methoxy)benzaldehyde (Compound (Ia)) and intermediates used in such processes. Compound (Ia) binds to hemoglobin and increases it oxygen affinity and hence can be useful for the treatment of diseases such as sickle cell disease.

BACKGROUND

Compound (Ia) is disclosed in Example 17 of the International Publication No. WO2013/102142. Compound (Ia) binds to hemoglobin and increases it oxygen affinity and hence can be useful for the treatment of diseases such as sickle cell disease.

In general, for a compound to be suitable as a therapeutic agent or part of a therapeutic agent, the compound synthesis must be amendable to large scale manufacturing and isolation. The large scale manufacturing and isolation should not impact the physical properties and purity of the compound nor should it negatively impact cost or efficacy of a formulated active ingredient. Accordingly, scale up of manufacturing and isolation may require significant efforts to meet these goals.

SUMMARY

Compound (Ia) has been synthesized by certain methods starting with 2,6-dihydroxbenzaldehyde (compound (1)) where each hydroxyl moiety is protected with an unbranched, straight-chain alkyl or alkoxyalkyl such as, for example, methyl or methoxymethyl. Following installation of the aldehyde group, various methods of deprotection of the hydroxyl group were employed to synthesize compound (1) used in the synthesis and production of Compound (Ia). However, the deprotection processes used lead to unwanted polymerization and decomposition reactions of compound (1)—attributed, in part, to the conditions used for deprotection of the hydroxy groups. The undesired byproducts yield complex mixtures, lower yields of Compound (Ia), and require significant effort to purify Compound (Ia) to a degree acceptable for use as a part of a therapeutic agent, thus rendering the above processes impractical for commercial scale synthesis of Compound (Ia).

Provided herein are processes for the synthesis of Compound (Ia):

(Ia)

that employ a protecting group sequence and mild reaction conditions to obtain compound (1) in a manner that suppresses unwanted polymerization and decomposition reactions and enables commercial scale synthesis of Compound (Ia).

In one aspect, provided is a process of synthesizing compound (1):

(1)

the process comprising:
Step (i): treating a compound of formula (2):

(2)

where each R is —CH(CH$_2$R$^1$)—OR$^2$ or tetrahydropyran-2-yl optionally substituted with one, two, or three alkyl with an acid to provide a compound (1) and wherein R$^1$ is hydrogen or alkyl and R$^2$ is alkyl;

Step (ii): optionally converting compound (1) to Compound (Ia):

(Ia)

by reacting compound (1) with a compound of formula (3):

where LG is a leaving group under alkylation reacting conditions; and

Step (iii): optionally crystallizing Compound (Ia) from heptane and methyl tert-butyl ether at 40°+/−5° C. to 55+/−5° C., preferably at 45°+/−5° C. to 55+/−5° C.

Further provided herein is a process for synthesizing Compound (Ia), the process comprising performing Steps (i) and (ii) of the first aspect in sequence, including embodiments and subembodiments of aspect 1 described herein, thereby synthesizing Compound (Ia). Further provided herein is a process for synthesizing Compound (Ia), the process comprising performing Steps (i), (ii), and (iii) of the first aspect in sequence, including embodiments and subembodiments of aspect 1 described herein, thereby obtaining Compound (Ia).

Provided herein in a second aspect, is a process of synthesizing a compound of formula (2):

the process comprising formylating a compound of formula (4):

wherein each R in compounds of formulae (2) and (4) is —CH(CH$_2$R$^1$)—OR$^2$ (where R$^1$ is hydrogen or alkyl and R$^2$ is alkyl) or tetrahydropyran-2-yl optionally substituted with one, two, or three alkyl to provide a compound of formula (2) above.

Provided herein in a third aspect, is a process of synthesizing a compound of formula (4):

wherein each R is —CH(CH$_2$R$^1$)—OR$^2$ (wherein R$^1$ is hydrogen or alkyl and R$^2$ is alkyl) or tetrahydropyran-2-yl optionally substituted with one, two, or three alkyl, the process comprising:

reacting compound (5):

with a vinyl ether of formula CHR$^1$=CHOR$^2$ (wherein R$^1$ is hydrogen or alkyl and R$^2$ is alkyl) or 3,4-dihydro-2H-pyran optionally substituted with one, two or three alkyl, in the presence of a weak acid to provide a compound of formula (4) above.

Provided in a fourth aspect is a process of synthesizing compound (1):

wherein each R is —CH(CH$_2$R$^1$)—OR$^2$ (where R$^1$ is hydrogen or alkyl and R$^2$ is alkyl) or tetrahydropyran-2-yl optionally substituted with one, two, or three alkyl, the process comprising:

Step (a): reacting compound (5):

with a vinyl ether of formula CHR$^1$=CHOR$^2$ (wherein R$^1$ is hydrogen or alkyl and R$^2$ is alkyl) or 3,4-dihydro-2H-pyran optionally substituted with one, two or three alkyl, in the presence of a weak acid to provide a compound of formula (4):

wherein each R is —CH(CH$_2$R$^1$)—OR$^2$ (where R$^1$ is hydrogen or alkyl and R$^2$ is alkyl) or tetrahydropyran-2-yl optionally substituted with one, two, or three alkyl;

Step (b): treating compound (4) in situ with a formylating agent to provide a compound of formula (2):

(2)

Step (c): treating the compound of formula (2) in situ with an acid to provide compound (1) above;

Step (d): optionally converting compound (1) to Compound (Ia):

(Ia)

by reacting compound (1) with a compound of formula (3)

(3)

where LG is a leaving group under alkylation reacting conditions; and

Step (e): optionally crystallizing Compound (Ia) from heptane and methyl tert-butyl ether at 40°+/−5° C. to 55+/−5° C., preferably at 45°+/−5° C. to 55+/−5° C.

Further provided herein is a process of synthesizing Compound (Ia), the process comprising performing Steps (a), (b), and (c) or (b) and (c) of the fourth aspect in sequence, including embodiments and subembodiments of aspect 4 described herein. Further provided herein is a process of synthesizing Compound (Ia), the process comprising performing Steps (a), (b), (c), and (d), or (b), (c), and (d) of the fourth aspect in sequence, including embodiments and subembodiments of aspect 4 described herein. Further provided herein is a process of synthesizing Compound (Ia), the process comprising performing Steps (a), (b), (c), (d), and (e), or (b), (c), (d) and (e) of the fourth aspect in sequence, including embodiments and subembodiments of aspect 4 described herein. In one embodiment, the first and fourth aspects further include synthesizing compound (3) from the intermediate compound (6) as provided in the seventh aspect described herein.

Further provided herein in a fifth aspect is an intermediate of the compound of formula (4):

(4)

where each R is tetrahydropyran-2-yl optionally substituted with one, two, or three alkyl.

In a sixth aspect, provided is an intermediate of formula (2):

(2)

where each R is —CH(CH$_2$R$^1$)—OR$^2$ (wherein R$^1$ is hydrogen or alkyl and R$^2$ is alkyl) or tetrahydropyran-2-yl optionally substituted with one, two, or three alkyl.

In a seventh aspect, provided is a process of synthesizing compound (6):

(6)

the process comprising reacting a boronic acid compound of formula:

where R$^3$ and R$^4$ are independently alkyl or together form —(CR'R")$_2$— where R' and R" are independently alkyl; with where X is halo or triflate, in the presence of a palladium catalyst and a base in an organic/aqueous reaction mixture. Compound (6) can be used in the synthesis of Compound (3) as described herein.

The above aspects can be understood more fully by reference to the detailed description and examples below, which are intended to exemplify non-limiting embodiments.

DETAILED DESCRIPTION

Unless otherwise stated, the following terms as used in the specification and claims are defined for the purposes of this Application and have the following meaning:

"Alkyl" means a linear saturated monovalent hydrocarbon radical of one to six carbon atoms or a branched saturated monovalent hydrocarbon radical of three to six carbon atoms, e.g., methyl, ethyl, propyl, 2-propyl, butyl, pentyl, and the like.

"Optional" or "optionally" means that the subsequently described event or circumstance may but need not occur, and that the description includes instances where the event or circumstance occurs and instances in which it does not. For example, "optionally crystallizing Compound (Ia) from heptane and methyl tert-butyl ethyl" means that the crystallization may but need not be done.

"About" as used herein means that a given amount or range includes deviations in range or amount that fall within experimental error unless indicated otherwise.

"Substantially pure" as used herein in connection with the polymorphic form refers to a compound such as Compound (Ia) wherein at least 70% by weight of the compound is present as the given polymorphic form. For example, the phrase "Compound (Ia) is substantially pure Form I or II" refers to a solid state form of Compound (Ia) wherein at least 70% by weight of Compound (Ia) is in Form I or II respectively. In one embodiment, at least 80% by weight of Compound (Ia) is in Form I or II respectively. In another embodiment, at least 85% by weight of Compound (Ia) is in Form I or II respectively. In yet another embodiment, at least 90% by weight of Compound (Ia) is in Form I or II respectively. In yet another embodiment, at least 95% by weight of Compound (Ia) is in Form I or II respectively. In yet another embodiment, at least 99% by weight of Compound (Ia) is in Form I or II respectively.

EMBODIMENTS (a) In embodiment (a), the process of the first aspect further comprises formylating a compound of formula (4):

(4)

wherein each R is —CH(CH$_2$R$^1$)—OR$^2$ wherein R$^1$ is hydrogen or alkyl and R$^2$ is alkyl or R is tetrahydropyran-2-yl optionally substituted with one, two, or three alkyl to provide a compound of formula (2).

(2)

In a first subembodiment of embodiment (a), each R is the same. In a second subembodiment, the tetrahydropyran-2-yl moiety is unsubstituted. In a third subembodiment of embodiment (a), the tetrahydropyran-2-yl moiety is substituted with one, two, or three alkyl.

(b) In embodiment (b) the process of embodiment (a) further comprises reacting compound (5):

(5)

with a vinyl ether of formula CHR$^1$=CHOR$^2$, where R$^1$ is hydrogen or alkyl and R$^2$ is alkyl) or 3,4-dihydro-2H-pyran optionally substituted with one, two or three alkyl, in the presence of a weak acid to provide a compound of formula (4):

(4)

wherein each R is —CH(CH$_2$R$^1$)—OR$^2$ (where R$^1$ is hydrogen or alkyl and R$^2$ is alkyl) or tetrahydropyran-2-yl optionally substituted with one, two, or three alkyl.

In one subembodiment of embodiment (b), the 3,4-dihydro-2H-pyran moiety is unsubstituted. In another subembodiment of embodiment (b), the 3,4-dihydro-2H-pyran moiety is substituted with one, two or three alkyl.

(c) In embodiment (c), the process of the first aspect, Step (i), fourth aspect, Step (c), and embodiments (a) and (b) is wherein the acid used in the removal of R group is an organic or inorganic acid. In a first subembodiment of embodiment (c), the acid is hydrochloric acid, sulfuric acid, trifluoroacetic acid, methanesulfonic acid, or ethanesulfonic acid. In a second subembodiment of embodiment (c), the acid is hydrochloric acid. In a third subembodiment of embodiment (c), including subembodiments and embodiments contained therein, the reaction is performed at a pH of less than about: 4, 3, 2, or 1. In a fourth subembodiment of embodiment (c), including subembodiments and embodiments contained therein, the reaction is performed at a pH of about 1 to about 3. In a fifth subembodiment of embodiment (c), including subembodiments and embodiments contained therein, the reaction is performed at a pH greater than 1. In a sixth subembodiment of embodiment (c), including subembodiments and embodiments contained therein, the reaction is performed at a pH less than 1. In a seventh subembodiment of embodiment (c), including subembodiments and embodiments contained therein, the compound (2) is treated in-situ with the organic or inorganic acid to synthesize compound (1). In an eight subembodiment of embodiment (c), including subembodiments and embodiments contained therein, the reaction is carried out in an organic solvent such as tetrahydrofuran, methyl tetrahydrofuran, ethyl ether, or dioxane. In a ninth subembodiment of embodiment (c), including subembodiments and embodiments contained therein, the reaction is carried out in an organic solvent such as tetrahydrofuran. In a tenth subembodiment of embodiment (c), including subembodiments and embodiments contained therein, the reaction is carried out at temperatures less than 30° C.+/−5° C., preferably the reaction is carried out at temperatures less than about 20° C. In an eleventh subembodiment of embodiment (c), including subembodiments and embodiments contained therein, the deprotection is performed in a shorter amount of time than previous synthetic routes. The shortened deprotection time can reduce polymerization or decomposition of the intermediate compound (1) and/or, (2) as described herein.

(d) In embodiment (d), the process of the first and fourth aspects, embodiments (a), (b) and (c) and subembodiments contained therein, is wherein LG is chloro, bromo, tosylate, mesylate, or triflate. LG can preferably be chloro. In a first subembodiment of embodiment (d), LG is chloro and the reaction is carried out in the presence of a non-nucleophilic organic base (such as pyridine, trimethylamine, N-methyl-2-pyrrolidone, and diisopropylethylamine in the presence of a weak inorganic base such as sodium bicarbonate, potassium bicarbonate, cesium carbonate, and the like). In a second subembodiment of embodiment (d), the weak inorganic base is sodium bicarbonate. In a third subembodiment of embodiment (d), LG is chloro and the reaction is carried out in the presence of pyridine and a weak inorganic base such as sodium bicarbonate. In a fourth subembodiment of embodiment (d) and subembodiments and embodiments contained therein, the reaction is carried out in N-methyl-2-pyrrolidinone. In a fifth subembodiment of embodiment (d), LG is chloro and the reaction is carried out in N-methyl-2-pyrrolidinone in the presence of sodium bicarbonate and catalytic amount of NaI. In a sixth sub-embodiment of the embodiment (d) and sub-embodiments contained therein, the reaction is carried out at between 40° C. to 50° C. In a seventh sub-embodiment of the embodiment (d) and sub-embodiments contained therein, the reaction is carried out at between 43° C. to 45° C. In an eight sub-embodiment of the embodiment (d) and sub-embodiments contained therein, after the reaction is complete, the reaction mixture is treated with water and then seeded with Compound (Ia) Form I at 40° C. to 50° C., preferably 40° to 46° C. to give Compound (Ia) as substantially pure Form I, preferably Compound (Ia) is at least 95% by weight pure Form I.

(e) In embodiment (e), the process of the first aspect, Step (iii), fourth aspect Step (e) and embodiments (a), (b), (c) and (d) and subembodiments contained therein is wherein-, the crystallization of Compound (Ia) is carried out at 45+/−5° C. to 55+/−5° C. or at 45° C. to 55° C., and the solvent is n-heptane and methyl tert-butyl ether to provide substantially pure Compound (Ia) Form II. In one embodiment, at least 95% by wt of Compound (Ia) is Form II. In one embodiment, at least 98% by wt of Compound (Ia) is Form II. In one embodiment, at least 99% by wt of Compound (Ia) is Form II.

(f) In embodiment (f), the process of the first, second, third, fourth, fifth, and sixth aspects, embodiments (a)-(e), and subembodiments contained therein is wherein, each R is —CH(CH$_3$)—O—CH$_2$CH$_3$, —CH(C$_2$H$_5$)—O—CH$_2$CH$_3$. In one subembodiment of (g), each R is —CH(CH$_3$)—O—CH$_2$CH$_3$.

(g) In embodiment (g), the process of the first, second, third, fourth, fifth, and sixth aspects, embodiments (a)-(e), and subembodiments contained therein is wherein, each R is tetrahydropyran-2-yl optionally substituted with one or two methyl. In a first subembodiment of (g), R is tetrahydrofuran-2-yl. In a second subembodiment of (g), each R is tetrahydropyran-2-yl substituted with one methyl.

(h) In embodiment (h), the process of the third and fourth aspects, embodiments (a)-(e), and subembodiments contained therein is wherein, the acid used in the conversion of compound (5) to the compound of formula (4) is a weak acid such as p-toluenesulfonic acid or pyridinium tosylate. In a first subembodiment of embodiment (h), the acid is pyridinium tosylate.

(i) In embodiment (i) the process of second aspect and fourth aspect, Step (b), embodiments (a)-(i) and subembodiments contained therein, is wherein the formylating agent is n-BuLi and DMF, or n-formylmorpholine. In a first subembodiment of embodiment (i), the formylating agent is n-BuLi and DMF. In a second subembodiment of embodiment (i), including the first subembodiment of embodiment (i), the reaction is carried out in THF.

(j) In embodiment (j) the process of the seventh aspect, is wherein the palladium catalyst is dichloro[1,1'-bis(diphenylphosphino)ferrocene]palladium(II) or its dichloromethane adduct. In a first subembodiment of embodiment (j), R$^3$ and R$^4$ together form —C(CH$_3$)$_2$—C(CH$_3$)$_2$— and X is halo. In a second subembodiment of embodiment (j), including the first subembodiment of embodiment (j), R$^3$ and R$^4$ together form —C(CH$_3$)$_2$—C(CH$_3$)$_2$— and X is chloro.

(k) In embodiment (j) the intermediate of the fifth and sixth aspects is wherein each R is —CH(CH$_3$)—O—CH$_2$CH$_3$.

(l) In embodiment (l) the intermediate of the fifth and sixth aspects is wherein, each R is tetrahydropyran-2-yl.

Figure 1:
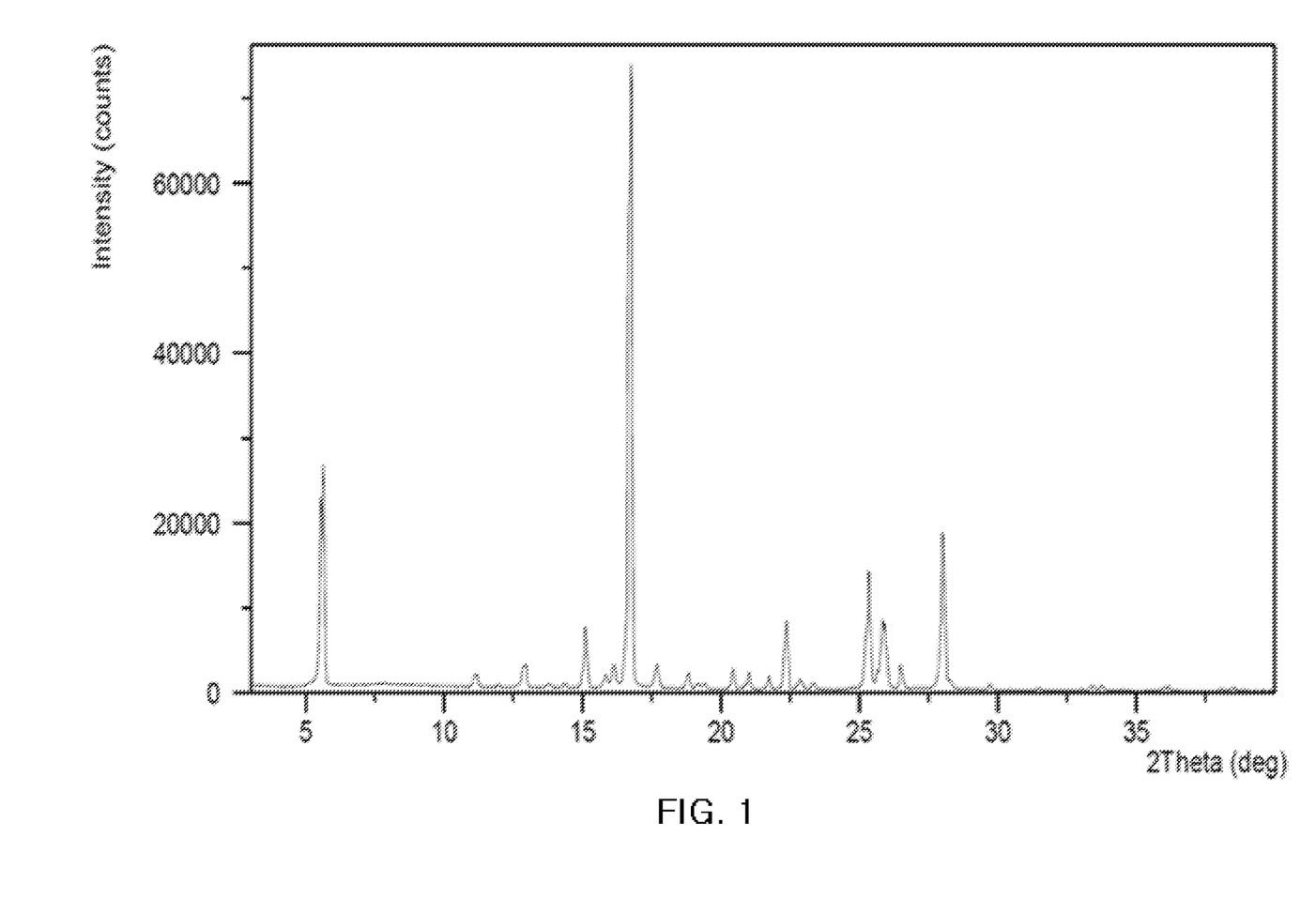
FIG. 1 is a XRPD pattern for crystalline Form I of Compound (Ia).

Form I of Compound (Ia) can be characterized by a XRPD pattern comprising X-ray powder diffraction peak (Cu Kα radiation) at one or more of 12.94°, 15.82°, 16.11°, 16.74°, 17.67°, 25.19°, 25.93° and 26.48°±0.2 °2θ. In one embodiment, Form I of Compound (Ia) is characterized by an X-ray powder diffraction pattern (Cu Kα radiation) substantially similar to that of FIG. 1. In another embodiment, the Form I of the free base of Compound (Ia) is characterized by a XRPD pattern comprising at least two X-ray powder diffraction peaks (Cu Kα radiation) selected from 12.94°, 15.82°, 16.11°, 16.74°, 17.67°, 25.19°, 25.93° and 26.48° (each ±0.2 °2θ). In another embodiment, the Form I of Compound (Ia) is characterized by a XRPD pattern comprising at least three X-ray powder diffraction peaks (Cu Kα radiation) selected from 12.94°, 15.82°, 16.11°, 16.74°, 17.67°, 25.19°, 25.93° and 26.48° (each ±0.2 °2θ). In another embodiment, Form I is characterized by a XRPD pattern comprising 1, 2, 3, 4, or more peaks as tabulated below in Table 1 that lists the XRPD peak positions and relative intensities of major XRPD peaks for Form I of Compound (Ia).

TABLE 1

XRPD peaks for Form I of Compound (Ia).

| °2θ | d space (Å) | Intensity (%) |
|---|---|---|
| 5.51 ± 0.20 | 16.045 | 31.1 |
| 5.63 ± 0.20 | 15.696 | 35.5 |
| 11.17 ± 0.20 | 7.923 | 2.05 |
| 12.94 ± 0.20 | 6.841 | 3.7 |
| 15.09 ± 0.20 | 5.870 | 9.8 |

TABLE 1-continued

XRPD peaks for Form I of Compound (Ia).

| °2θ | d space (Å) | Intensity (%) |
|---|---|---|
| 15.82 ± 0.20 | 5.600 | 2.3 |
| 16.11 ± 0.20 | 5.500 | 4.0 |
| 16.74 ± 0.20 | 5.295 | 100 |
| 17.67 ± 0.20 | 5.018 | 4.01 |
| 18.81 ± 0.20 | 4.716 | 2.8 |
| 19.13 ± 0.20 | 4.639 | 0.9 |
| 19.38 ± 0.20 | 4.581 | 1.0 |
| 20.41 ± 0.20 | 4.350 | 3.4 |
| 21.00 ± 0.20 | 4.230 | 2.9 |
| 21.72 ± 0.20 | 4.092 | 2.2 |
| 22.36 ± 0.20 | 3.976 | 10.6 |
| 22.86 ± 0.20 | 3.890 | 1.7 |
| 23.30 ± 0.20 | 3.817 | 1.2 |
| 25.19 ± 0.20 | 3.54 | 7.9 |
| 25.33 ± 0.20 | 3.516 | 19.1 |
| 25.93 ± 0.20 | 3.436 | 8.7 |
| 26.48 ± 0.20 | 3.366 | 3.6 |
| 28.01 ± 0.20 | 3.185 | 24.8 |
| 28.27 ± 0.20 | 3.157 | 1.49 |

Figure 2:
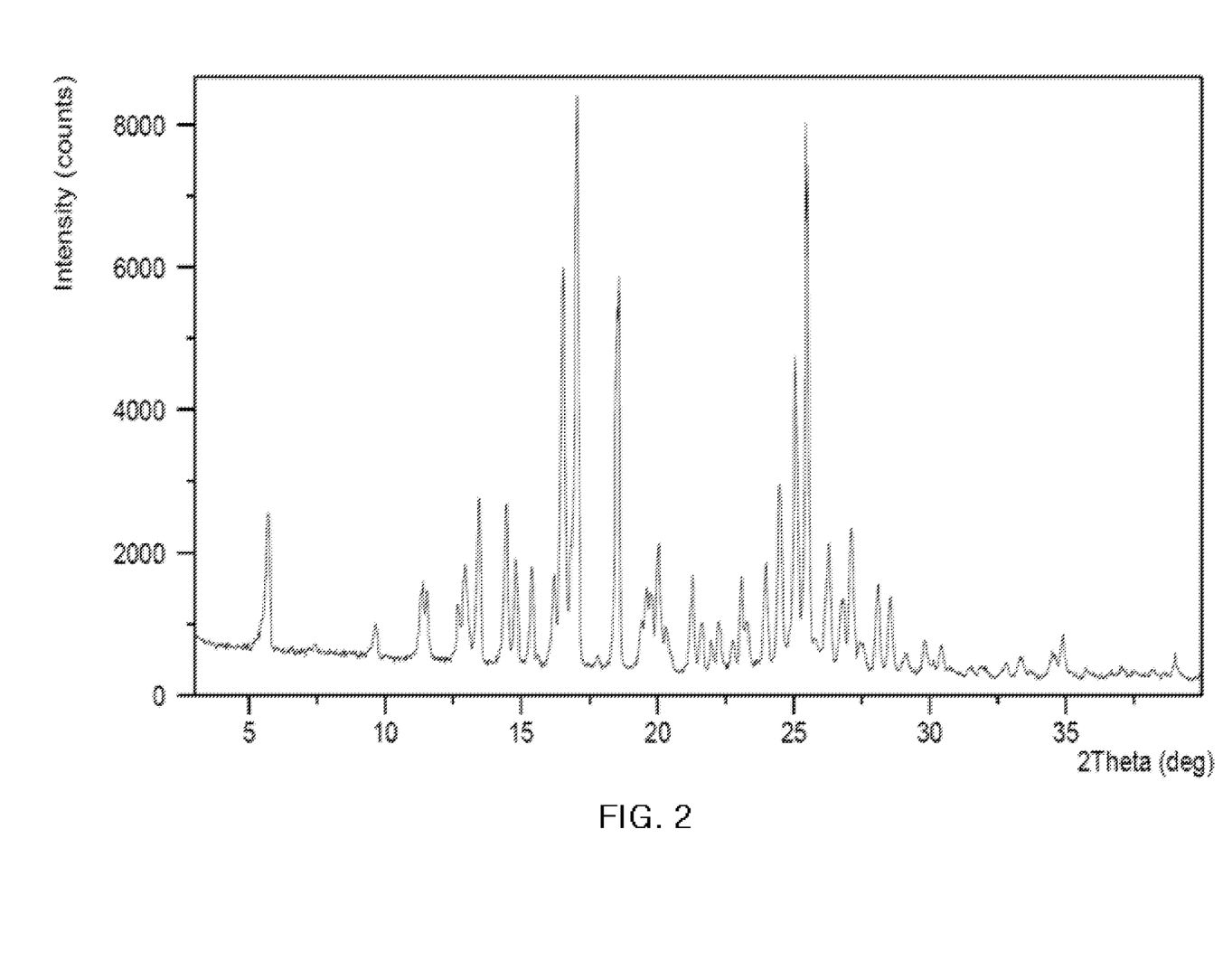
FIG. 2 is a XRPD pattern for crystalline Form II of Compound (Ia).

Form II of Compound (Ia) can be characterized by a XRPD pattern comprising a X-ray powder diffraction peak (Cu Kα radiation at one or more of 13.44°, 14.43°, 19.76°, 23.97°±0.2 °2θ. In another embodiment, Form II of Compound (Ia) is characterized by a XRPD pattern comprising a X-ray powder diffraction pattern (Cu Kα radiation) substantially similar to that of FIG. 2. In another embodiment, Form II of Compound (Ia) is characterized by a XRPD pattern comprising at least two X-ray powder diffraction peak (Cu Kα radiation) selected from 13.44°, 14.43°, 19.76°, 23.97 °2θ (each ±0.2 °2θ). In another embodiment, Form II of Compound (Ia) is characterized by a XRPD pattern comprising at least three X-ray powder diffraction peaks (Cu Kα radiation) selected from 13.44°, 14.43°, 19.76°, and 23.97 °2θ (each ±0.2 °2θ). In another embodiment, Form II of Compound (Ia) is characterized by a XRPD pattern comprising X-ray powder diffraction peaks (Cu Kα radiation) selected from 13.44°, 14.43°, 19.76°, and 23.97 °2θ (each ±0.2 °2θ).

In another embodiment, Form II is characterized by 1, 2, 3, 4, or more peaks as tabulated below in Table 2 that lists the XRPD peak positions and relative intensities of major XRPD peaks for Form II of Compound (Ia).

TABLE 2

Major XRPD peaks for Form II of Compound (Ia).

| °2θ | d space (Å) | Intensity (%) |
|---|---|---|
| 5.70 ± 0.20 | 15.494 | 24.8 |
| 9.64 ± 0.20 | 9.172 | 5.4 |
| 11.32 ± 0.20 | 7.812 | 12.2 |
| 11.52 ± 0.20 | 7.680 | 12.2 |
| 12.66 ± 0.20 | 6.992 | 10.3 |
| 12.90 ± 0.20 | 6.861 | 16.4 |
| 13.44 ± 0.20 | 6.587 | 28.5 |
| 14.43 ± 0.20 | 6.137 | 28.7 |
| 14.79 ± 0.20 | 5.991 | 18.3 |
| 15.38 ± 0.20 | 5.761 | 17.5 |
| 16.18 ± 0.20 | 5.477 | 16.4 |
| 16.51 ± 0.20 | 5.370 | 72.3 |
| 17.04 ± 0.20 | 5.205 | 100 |
| 18.56 ± 0.20 | 4.781 | 71.1 |
| 20.01 ± 0.20 | 4.437 | 22.5 |
| 20.31 ± 0.20 | 4.373 | 7.7 |
| 23.06 ± 0.20 | 3.858 | 16.3 |
| 23.97 ± 0.20 | 3.712 | 19.7 |
| 24.46 ± 0.20 | 3.639 | 34.1 |

TABLE 2-continued

Major XRPD peaks for Form II of Compound (Ia).

| °2θ | d space (Å) | Intensity (%) |
|---|---|---|
| 25.06 ± 0.20 | 3.554 | 53.6 |
| 25.45 ± 0.20 | 3.500 | 88.0 |
| 26.29 ± 0.20 | 3.390 | 23.5 |
| 26.78 ± 0.20 | 3.329 | 12.6 |
| 27.07 ± 0.20 | 3.294 | 26.2 |
| 27.49 ± 0.20 | 3.245 | 5.4 |
| 28.09 ± 0.20 | 3.176 | 15.6 |
| 28.54 ± 0.20 | 3.128 | 13.44 |

The processes described herein can be used for synthesizing Compound (Ia) at a manufacturing scale synthesis (e.g., at least 0.05, 0.1, 0.2, 0.3, 0.4, 0.5, 1, 2, 3, 4, 5, 10, 20, 25, 50, 100, or more kg amounts). The processes described herein can be useful for larger scale syntheses (e.g., at least 0.05, 0.1, 0.2, 0.3, 0.4, 0.5, 1, 2, 3, 4, 5, 10, 20, 25, 50, 100, or more kg amounts) which retain the physical properties, purity, efficacy, a combination thereof, or all thereof, of Compound (Ia).

The processes described herein surprisingly reduce polymerization of compound (1) and surprisingly reduce polymerization intermediates during the synthesis of Compound (Ia). In one embodiment, the polymerization can be reduced by at least 5%, 10%, 20%, 25%, 50%, 75%, 80%, 90%, 95% or more compared to previous synthesis routes as described herein.

The processes described herein surprisingly reduce decomposition reactions during the synthesis of (and deprotection of) compound (1). The decomposition reactions can be reduced by at least 5%, 10%, 20%, 25%, 50%, 75%, 80%, 90%, 95% or more compared to previous synthesis routes as described herein. The processes described herein can increase the purity of the final product of Compound (Ia) by at least 5%, 10%, 20%, 25%, 50%, 75%, 80%, 90%, 95%, 97%, 99% or more compared to previous synthesis routes as described herein.

XRPD Analysis:

XRPD patterns were collected with a PANalytical X'Pert3 X-ray Powder Diffractometer using an incident beam of Cu Kα radiation (Kα1 (Å): 1.540598, Kα2 (Å): 1.544426 Kα2/Kα1 intensity ratio: 0.50, tube setting at 45 kV, 40 mA). A continuous scan mode between 3 and 40 (°2Θ) with a scan speed of 50 s per step and a step size of 0.0263 (°2Θ) in reflection mode was used. The diffractometer was configured using the symmetric Bragg-Brentano geometry. Data collection used Data Collector Version® 4.3.0.161 and Highscore Plus® version 3.0.0.

EXAMPLES

Example 1

Synthesis of 2,6-dihydroxybenzaldehyde (Compound (1))

(1)

Step 1:

Tetrahydrofuran (700 mL) was added to resorcinol (170 g, 1.54 mol, 1 eq.) under inert gas protection, followed by addition of pyridinium tosylate (3.9 g, 15.4 mmol, 0.01 eq.), THF 65 mL) and the reaction mixture was cooled down to 0-5° C. Within 1-1.5 h ethylvinyl ether (444 mL, 4.63 mol, 3.0 eq.) was added while maintaining a temperature ≤5° C. After the addition was complete the reaction mixture was allowed to reach room temperature within 1.5 h. The reaction was stirred overnight, cooled down to 10-15° C., and 510 mL of ½ sat. NaHCO$_3$ was added while maintaining the reaction solution below 20° C. The phases were separated. The organic phase was washed once with 425 mL of water and once with 425 mL 12.5% NaCl solution and evaporated and azeotroped with THF to give bis-EOE-protected resorcinol (401.2 g, 1.55 mol, 102% uncorrected) as a clear colorless to yellowish oil.

Step 2:

Bis-EOE-protected resorcinol (390 g of, actual: 398.6 g=1.53 mol, 1 eq., corrected to 100% conversion) was added under inert gas protection to a 6 L glass vessel and THF (1170 mL) was added. The reaction mixture was cooled down to −10° C. to −5° C. and n-BuLi (625 mL, 2.7 M in heptane, 1.687 mol, 1.1 eq.) was added. The reaction mixture was agitated at −5° C.-0° C. for 30-40 min and then DMF (153.4 mL, 1.99 mmol, 1.3 eq.) was added starting at −10° C. to −5° C. The reaction mixture was stirred until complete and then quenched with 1N HCl/EtOAc. It was also discovered, inter alia, that protection with the EOE groups not only resulted in less byproducts but appeared to increase the speed of the formylation reaction to provide 2,6-bis(1-ethoxyethoxy)benzaldehyde (compound (2)).

The mixture was worked up, phase separated and the aqueous washed with MTBE. After aqueous wash to remove salts the organic phase was concentrated to the neat oil to obtain the compound (2) as yellow oil (almost quantitative).

A batch preparation was performed using solvent swap and was completed faster than other known methods for synthesizing Compound (Ia) with better purity and yield. The deprotection sequence allowed in-situ use of compound (2).

Step 3:

To the reaction solution of Step 2 was added 1N HCl (1755 mL) while maintaining the temperature <20° C. The pH was of the solution was adjusted to pH=0.7-0.8 with 6 M HCl. The reaction mixture was stirred for 16 h. After the reaction was complete the organic phase was separated and 1560 mL of methyl tert butyl ether was added. The organic phase was washed once with 1170 mL of 1N HCl, once with 780 mL of ½ sat. NaCl solution and once with 780 mL of water and then concentrated to a volume of ~280 mL. To the solution was added 780 mL of methyl tert butyl ether and concentrate again to 280 mL [temperature <45° C., vacuo]. To the slurry was added 780 mL of acetonitrile and the solution was concentrated in vacuo at T<45° C. to a final volume of ~280 mL. The slurry was heated to re-dissolve the solids. The solution was cooled slowly to RT and seeded at 60-65° C. to initiate crystallization of the product. The slurry was cooled down to −20° C. to −15° C. and agitated at this temperature for 1-2 h. The product was isolated by filtration and washed with DCM (pre-cooled to −20° C. to −15° C.) and dried under a stream of nitrogen to give 2,6-dihydroxybenzaldehyde as a yellow solid. Yield: 138.9 g (1.00 mol, 65.6%).

Example 1A

Alternate Synthesis of 2,6-dihydroxybenzaldehyde Compound (1)

Step 1:

In a suitable reactor under nitrogen, tetrahydrofuran (207 L) was added to resorcinol (46 kg, 0.42 kmol, 1 eq.) followed by addition of pyridinium tosylate (1.05 kg, 4.2 mol, 0.01 eq.), and the reaction mixture was cooled down to 0-5° C. Within 1-1.5 h ethylvinyl ether (90.4 kg, 120.5 L, 125 kmol, 3.0 eq.) was added while maintaining a temperature ≤5° C. After the addition was complete the reaction mixture was allowed to reach room temperature within 1.5 h. The reaction was stirred overnight, cooled down to 10-15° C., and 138 L of aqueous 4% NaHCO$_3$ was added while maintaining the reaction solution below 20° C. The phases were separated. The organic phase was washed once with 115 L of water and once with 125.2 kg of a 12.5% NaCl solution. The organic layer was dried by azeotropic distillation with THF to a water content value <0.05% (by weight) to yield bis-EOE-protected resorcinol (106.2 kg, 0.42 kmol) as a solution in THF. An advantage over previously reported protection procedures is that the bis-EOE-protected resorcinol product does not need to be isolated as a neat product. The product-containing THF solution can be used directly in the next reaction step thus increasing throughput and reducing impurity formation.

Step 2:

Bis-EOE-protected resorcinol solution (assumption is 100% conversion) was added under inert gas protection to suitable reactor. The reaction mixture was cooled down to −10° C. to −5° C. and n-BuLi (117.8 kg, 25% in heptane, 1.1 eq.) was added. The reaction mixture was agitated at −5° C.-0° C. for 30-40 min and then DMF (39.7 kg, 0.54 kmol, 1.3 eq.) was added at −10° C. to −5° C. The reaction mixture was stirred until complete and then quenched with aqueous HCl (1M, 488.8 kg) to give 2,6-bis(1-ethoxyethoxy)benzaldehyde. An advantage over previously reported procedures of using EOE protecting group is that the HCl quenched solution can be used directly in the deprotection step, and 2,6-bis(1-ethoxyethoxy)benzaldehyde does not need to be isolated as a neat oil.

Step 3:

The pH of the quenched solution was adjusted to <1 with aqueous HCl (6M, ca 95.9 kg) and the reaction mixture stirred at ambient temperature for 16 h. After the reaction was complete the organic phase was separated and 279.7 kg of methyl tert butyl ether was added. The organic phase was washed once with aqueous 1N HCl (299 kg), once with aqueous 12.5% NaCl (205.8 kg) and once with 189 kg of water and then concentrated to a volume of ca. 69 L. To the slurry was added 164 kg of acetonitrile and the solution was concentrated in vacuo at T<45° C. to a final volume of ca. 69 L. The slurry was heated to re-dissolve the solids. The solution was seeded at 60-65° C. to initiate crystallization of the product and cooled slowly to RT over 8 hrs. The slurry was cooled down to −20° C. to −15° C. and agitated at this temperature for 1-2 h. The product was isolated by filtration and washed with DCM (50.3 kg, pre-cooled to −20° C. to −15° C.) and dried under a stream of nitrogen to yield 2,6-dihydroxybenzaldehyde as a yellow solid. Yield: 37.8 kg (0.27 kmol, 65.4% Yield). The described telescoped approach from deprotection to crystallization increases the throughput and integrity of the product.

Example 2

Synthesis of 3-(chloromethyl)-2-(1-isopropyl-1H-pyrazol-5-yl)pyridine dihydrochloride salt Step 1:

An appropriately sized flask was purged with nitrogen and charged with (2-chloropyridin-3-yl)methanol (1.0 equiv), sodium bicarbonate (3.0 equiv), [1, 1′-bis(diphenyl-phosphino)-ferrocene]dichloropalladium (5 mol %), 1-isopropyl-5-(4,4,5,5-tetramethyl-1,3,2-dioxaborolan-2-yl)-1H-pyrazole (1.2 equiv), and a mixture of 2-MeTHF (17.4 vol) and deionized water (5.2 vol). The resulting solution was heated to 70° C. to 75° C. and conversion monitored by HPLC. Once the reaction was complete, the reaction mixture was cooled to room temperature, diluted with deionized water, and the phases were separated. The organic layer was extracted with 2 N HCl (10 vol) and the phases were separated. The aqueous phase was washed with MTBE. The pH of the aqueous phase was adjusted to 8-9 with 6 N NaOH. The product was extracted into EtOAc, treated with Darco G-60 for 30 to 60 min, dried over MgSO₄, filtered through Celite®, and concentrated to give (2-(1-isopropyl-1H-pyrazol-5-yl)pyridin-3-yl)methanol as a brown oil.

Step 2:

A suitably equipped reactor was charged with (2-(1-isopropyl-1H-pyrazol-5-yl)pyridin-3-yl)methanol hydrochloride salt (1 equivalent) and purified water. An aqueous sodium bicarbonate solution (8% NaHCO₃) was added slowly to maintain the solution temperature between 17° C. to 25° C. After addition was complete, the reaction mixture was stirred at 17° C. to 25° C. and dichloromethane was added and the organic layer was separated. DCM solution was then distilled under atmospheric conditions at approximately 40° C. and the volume was reduced. DCM was added the reactor and the contents of the reactor are stirred at 20° C. to 30° C. until a clear solution is formed. The contents of the reactor were cooled to 0° C. to 5° C. and thionyl chloride was charged to the reactor slowly to maintain a temperature of ≤5° C. The reaction solution was stirred at 17° C. to 25° C. When the reaction was complete, a solution of HCl (g) in 1,4-dioxane (ca. 4 N, 0.8 equiv.) was charged to the reactor slowly to maintain the solution temperature between 17° C. and 25° C. The product 3-(chloromethyl)-2-(1-isopropyl-1H-pyrazol-5-yl)pyridine dihydrochloride salt was filtered washed with dichloromethane and dried.

Example 3

Synthesis of 2-hydroxy-6-((2-(1-isopropyl-1H-pyrazol-5-yl)-pyridin-3-yl)methoxy)benzaldehyde (Compound (Ia)) Form I (Ia)

A suitably equipped reactor was charged with 3-(chloromethyl)-2-(1-isopropyl-1H-pyrazol-5-yl)pyridine dihydrochloride salt (1 equivalent), sodium iodide (0.05 equivalent), sodium bicarbonate (4 equivalent), 1-methyl-2-pyrrolidinone (NMP), and 2,6-dihydroxy-benzaldehyde (1 to 1.05 equiv.). The reaction mixture was heated slowly to 40° C. to 50° C. and stirred until the reaction was complete. Water was then added and the reaction mixture was cooled and maintained at 17° C. to 25° C. When the water addition was complete, the reaction mixture was stirred at 17° C. to 25° C. and slowly cooled to 0° C. to 5° C. and the resulting solids were collected by filtration. The solids were washed with a 0° C. to 5° C. 2:1 water/NMP solution, followed by 0° C. to 5° C. water. The solids were filtered and dried to give 2-hydroxy-6-((2-(1-isopropyl-1H-pyrazol-5-yl)-pyridin-3-yl)methoxy)benzaldehyde as Form I or a mixture of 2-hydroxy-6-((2-(1-isopropyl-1H-pyrazol-5-yl)-pyridin-3-yl)methoxy)benzaldehyde as Form I and NMP solvates.

Alternative Synthesis:

A suitably equipped reactor was charged with 3-(chloromethyl)-2-(1-isopropyl-1H-pyrazol-5-yl)pyridine bishydrochloride salt (1 equivalent), sodium iodide (0.05 equivalent), sodium bicarbonate (3 to 4 equivalent), 1-methyl-2-pyrrolidinone (7 equivalent, NMP), and 2,6-dihydroxybenzaldehyde (1.05 equivalent). The reaction mixture was heated to 40° C. to 50° C. and stirred until the reaction was complete. Water (5 equivalent) was then added while maintaining the contents of the reactor at 40° C. to 46° C. and the resulting clear solution seeded with 2-hydroxy-6-((2-(1-isopropyl-1H-pyrazol-5-yl)-pyridin-3-yl)methoxy)benzaldehyde Form I. Additional water (5 equivalent) was added while maintaining the contents of the reactor at 40° C. to 50° C., the reactor contents cooled to 15° C. to 25° C., and the reactor contents stirred for at least 1 hour at 15° C. to 25° C. The solids were collected, washed twice with 1:2 NMP: water and twice with water, and dried to yield 2-hydroxy-6-((2-(1-isopropyl-1H-pyrazol-5-yl)-pyridin-3-yl)methoxy)benzaldehyde Form I devoid of 2-hydroxy-6-((2-(1-isopropyl-1H-pyrazol-5-yl)-pyridin-3-yl)methoxy)benzaldehyde as NMP solvates.

Example 4

Preparation of 2-hydroxy-6-((2-(1-isopropyl-1H-pyrazol-5-yl)-pyridin-3-yl)methoxy)-benzaldehyde (Compound (Ia)) Form II (Ia)

Step 1:

A suitably equipped reactor with an inert atmosphere was charged with crude 2-hydroxy-6-((2-(1-isopropyl-1H-pyrazol-5-yl)-pyridin-3-yl)methoxy)benzaldehyde (from Example 3 above) and MTBE and the contents stirred at 17° C. to 25° C. until dissolution was achieved. The reaction solution was passed through a 0.45 micron filter and MTBE solvent volume reduced using vacuum distillation at approximately 50° C. The concentrated solution was heated to 55° C. to 60° C. to dissolve any crystallized product. When a clear solution was obtained, the solution was cooled to 50° C. to 55° C. and n-heptane was added. 2-Hydroxy-6-((2-(1-isopropyl-1H-pyrazol-5-yl)-pyridin-3-yl)methoxy)benzaldehyde (e.g., Form II) seeds in a slurry of n-heptane were charged and the solution was stirred at 50° C. to 55° C. The solution was cooled to 45° C. to 50° C. and n-heptane was added to the reactor slowly while maintaining a reaction solution temperature of 45° C. to 50° C. The reaction solution are stirred at 45° C. to 50° C. and then slowly cooled to 17° C. to 25° C. A sample was taken for FTIR analysis and the crystallization was considered complete when FTIR analysis confirmed 2-hydroxy-6-((2-(1-isopropyl-1H-pyrazol-5-yl)-pyridin-3-yl)methoxy)-benzaldehyde Form II. The contents of the reactor were then cooled to 0° C. to 5° C. and the solids were isolated and washed with cold n-heptane and dried.

What is claimed is:

1. A compound of formula (2):

(2)

wherein each R is —CH(CH$_2$R$^1$)OR$^2$; and
wherein each R$^1$ is independently hydrogen or alkyl, and each R$^2$ is independently alkyl.

2. The compound of claim 1, wherein each R is independently —CH(CH$_3$)—O—CH$_2$CH$_3$ or —CH(CH$_2$CH$_3$)—O—CH$_2$CH$_3$.

3. The compound of claim 1, wherein each R is —CH(CH$_3$)—O—CH$_2$CH$_3$.

4. The compound of claim 1, wherein each R is —CH(CH$_2$CH$_3$)—O—CH$_2$CH$_3$.

5. A method of preparing the compound of formula (2):

(2)

wherein each R is —CH(CH$_2$R$^1$)OR$^2$, and
wherein each R$^1$ is independently hydrogen or alkyl, and each R$^2$ is independently alkyl; comprising treating a compound of formula (4)

(4)

with a formylating agent to provide the compound of formula (2).

6. The method of claim 5, wherein the formylating agent is n-butyllithium (n-BuLi) and dimethylformamide (DMF).

7. The method of claim 5, wherein the formylating agent is N-formylmorpholine.

8. The method of claim 5, further comprising reacting compound (5):

(5)

with a vinyl ether of formula CHR$^1$=CHOR$^2$ in the presence of a weak acid to provide a compound of formula (4);
wherein the compound of formula (4) is treated in situ with the formylating agent to provide the compound of formula (2).

9. The method of claim 8, wherein the formylating agent is n-butyllithium and dimethylformamide.

10. The method of claim 8, wherein the formylating agent is N-formylmorpholine.

11. A compound of formula (2a):

(2a)

12. A method of preparing a compound of formula (2a)

(2a)

comprising treating a compound of formula (4a)

(4a)

with a formylating agent to provide the compound of formula (2a).

13. The method of claim 12, wherein the formylating agent is n-butyllithium and dimethylformamide.

14. The method of claim 12, wherein the formylating agent is N-formylmorpholine.

15. The method of claim 12, further comprising reacting compound (5):

(5)

with ethyl vinyl ether in the presence of a weak acid to provide a compound of formula (4a);

wherein the compound of formula (4a) is treated in situ with the formylating agent to provide the compound of formula (2a).

16. The method of claim 15, wherein the formylating agent is n-butyllithium and dimethylformamide.

17. The method of claim 15, wherein the formylating agent is N-formylmorpholine.

* * * * *